(12) United States Patent
Hammer et al.

(10) Patent No.: US 7,345,022 B2
(45) Date of Patent: Mar. 18, 2008

(54) ANTI-FIBRIL PEPTIDES

(75) Inventors: Robert P. Hammer, Baton Rouge, LA (US); Yanwen Fu, San Diego, CA (US); Tod J. Miller, Smyrna, TN (US); Mark L. McLaughlin, Tampa, FL (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 2 days.

(21) Appl. No.: 10/666,095

(22) Filed: Sep. 18, 2003

(65) Prior Publication Data

US 2005/0119187 A1 Jun. 2, 2005

Related U.S. Application Data

(60) Provisional application No. 60/412,081, filed on Sep. 19, 2002.

(51) Int. Cl.
*A61K 38/03* (2006.01)
*A61K 38/08* (2006.01)
*A61K 38/10* (2006.01)
*C07K 4/00* (2006.01)
*C07K 7/06* (2006.01)
*C07K 7/08* (2006.01)

(52) U.S. Cl. ............... 514/14; 514/2; 514/16; 514/17; 530/300; 530/327; 530/329

(58) Field of Classification Search ............ None
See application file for complete search history.

(56) References Cited

U.S. PATENT DOCUMENTS

| | | | |
|---|---|---|---|
| 5,854,204 A | 12/1998 | Findeis et al. | 514/2 |
| 6,277,826 B1 | 8/2001 | Findeis et al. | 514/17 |
| 6,566,334 B1 | 5/2003 | McLaughlin et al. | 514/14 |
| 6,689,753 B1 * | 2/2004 | Soto-Jara | 514/17 |

OTHER PUBLICATIONS

Conway et al. Emerging Beta-Amyloid Therapies for the Treatment of Alzheimer's Disease. Current Pharmaceutical Design. 2003, vol. 9, pp. 427-447.*

(Continued)

*Primary Examiner*—Jeffrey Edwin Russel
(74) *Attorney, Agent, or Firm*—John H. Runnels; Bonnie J. Davis

(57) ABSTRACT

Novel peptides are disclosed that may be used as inhibitors of amyloidogenesis, as suppressors of amyloid toxicity, and as therapeutic agents for amyloid-associated diseases such as Alzheimer's disease, Parkinson's Disease, Creutzfeldt-Jakob Disease, Huntington's Disease, and Type II Diabetes. These new β-strand mimics (β-sheet "blockers"), containing $C^{\alpha,\alpha}$-disubstituted amino acids, specifically interact with and block the development of the β-sheet structure of the developing fibrils of amyloid diseases, such as Alzheimer's disease amyloid β-peptide (Aβ). We have discovered that oligomerization of β-sheet structures, including those implicated in amyloid-associated diseases, may be inhibited or even reversed by the presence of extended peptide structures that have only one edge available for hydrogen bonding. Without a second edge that is also available for hydrogen bonding, the extension of a developing β-sheet is blocked by binding to the novel peptides.

24 Claims, 9 Drawing Sheets

H-Lys-Dibg-Val-Dbzg-Phe-Dpg-(Lys)$_6$-NH$_2$

OTHER PUBLICATIONS

H. LeVine. The Challenge of Inhibiting A-Beta Polymerization. Current Medicinal Chemistry. 2002, vol. 9, pp. 1121-1133.*

Aucoin, J., "Determination of Possible Surface Adsorption of Beta-Amyloid Aggregate Species and Aggregation Inhibition Products Using Scanning Force Microscopy and Dynamic Light Scattering," Presentation at National Meeting of the American Chemical Society (Aug. 18, 2002).

Aucoin, J., "Dissection of an Amyloid Aggregation Inhibitor," presentation at 225th American Chemical Society conference (Mar. 23-27, 2003).

Aucoin, J., "Interplay between beta-Amyloid (1-40) and a Peptide-based beta-Amyloid Aggregation Inhibitor," presentation at 225th American Chemical Society conference (Mar. 23-27, 2003).

Aucoin, J. et al., "Surface and Solution Studies of Beta-Amyloid Aggregation using Dynamic Light Scattering and Atomic Force Microscopy," Presentation at Pittsburgh Conference (Sep. 17, 2002).

Fu, "Facile Synthesis of Sterically Hindered $\alpha,\alpha$-Disubstituted Amino Acids and Their Incorporation into Peptides by Solid-Phase Peptide Synthesis,"Presentation at 222nd National Meeting of the American Chemical Society (Aug. 26, 2001).

Fu, Y., "Artificial Peptides Containing $C^{\alpha,\alpha}$-Disubstituted Amino Acids: Synthesis, Conformational Studies, and Application as $\beta$-Strand Mimics," PhD Dissertation, Louisiana State University (Baton Rouge, LA, submitted Dec. 2002).

Fu, Y. et al., "Efficient Acylation of the *N*-Terminus of Highly Hindered $C^{\alpha,\alpha}$-Disubstituted Amino Acids via Amino Acid Symmetrical Anhydrides," *Org. Lett.*, vol. 4, pp. 237-240 (2002).

Fu, Y. et al., "Sterically Hindered $C^{\alpha,\alpha}$-Disubstituted $\alpha$-Amino Acids: Synthesis from $\alpha$-Nitroacetate and Incorporation into Peptides," *J. Org. Chem.*, vol. 66, pp. 7118-7124 (2001).

Hammer, R. et al., "$\beta$-Strand Mimics as Fibrillogenesis Inhibitors," Excerpt from grant proposal submitted to National Institutes of Health (1999).

Pallitto, M. et al., "Recognition sequence design for peptidyl modulators of $\beta$-amyloid aggregation and toxicity," *Biochem.*, vol. 38, pp. 3570-3578 (1999).

Toniolo, C. et al., "Control of peptide conformation by the Thorpe-Ingold effect ($C^{\alpha}$-tetrasubstitution)," *Biopolymers*, vol. 60, pp. 396-419 (2001, or 2002).

Wilcock, D. et al., "Intracranially administered anti-A$\beta$ antibodies reduce $\beta$-amyloid deposition by mechanisms both independent of and associated with microglial activation," J. Neurosci., vol. 23, pp. 3745-3751 (2003).

Wysong, C. et al., "4-Aminopiperidine-4-carboxylic acid: A cyclic alpha, alpha-disubstitued amino acid for preparation of water-soluble highly helical peptides," *J. Org. Chem.*, vol. 61, pp. 7650-7651 (1996).

Aucoin, J., "Interplay between beta-Amyloid (1-40) and a Peptide-based beta-Amyloid Aggregation Inhibitor," abstract of presentation at 225th American Chemical Society conference (Mar. 23-27, 2000).

H. Ikeda et al., "Genome sequence of an industrial microorganism *Streptomyces avermitilis*: Deducing the ability of producing secondary metabolites," Proc. Natl. Acad. Sci. (USA), vol. 98, pp. 12215-12220 (2001).

* cited by examiner

H-Lys-Dibg-Val-Dbzg-Phe-Dpg-(Lys)₆-NH₂

ANTI-FIBRIL PEPTIDES

The benefit of the Sep. 19, 2002 filing date of provisional application Ser. No. 60/412,081, the complete disclosure of which is hereby incorporated by reference, is claimed under 35 U.S.C. § 119(e).

The development of this invention was partially funded by the Government under grant number 1 R01 AG17983-01 awarded by the National Institutes of Health. The Government has certain rights in this invention.

This invention pertains to the inhibition of amyloid fibrils with blocker peptides.

Several human diseases have been associated with the misfolding of proteins into insoluble fibrils having predominantly a β-sheet secondary structure. These diseases include Alzheimer's disease, Parkinson's disease, and Huntington's disease, and others. See Table 1. These diseases can be classified into three major types: (1) Familial diseases linked to genetic anomalies—e.g., point mutations in proteins that are directly involved in fibril formation, or mutations in proteins that control the processing or amount of an amyloidogenic protein. Examples of familial diseases include early onset Alzheimer's disease, early onset Parkinson's disease, Huntington's disease, and a range of other genetically-linked amyloid diseases. (2) More common are sporadic amyloid diseases that apparently result from an accumulation of amyloid over the lifetime of an individual, or sometimes from an accumulation associated with certain procedures such as hemodialysis. Examples include Alzheimer's and Parkinson's diseases, age-associated cardiac dysfunction, and type II diabetes mellitus. (3) Transmissible spongiform encephalopathies, diseases caused by exposure to exogenous prion proteins related to the PrP protein, such as kuru and mad cow disease.

TABLE 1

Amyloid Diseases and Associated Proteins

| Amyloid Disease | Associated Protein | Genetic link of the disease | Protein size in fibrils (kDa) |
|---|---|---|---|
| Alzheimer's disease | amyloid β-peptide | wild-type | 40–43 |
| Parkinson's disease | α-synuclein | wild-type | 35 |
| Creutzfeld-Jacob Disease (CJD) | PrP$^{Sc}$ | wild-type | 27–30 |
| Hemodialysis-associated amyloidosis | β$_2$-microglobulin | wild-type | 99 |
| Type II diabetes | amylin (i.e., IAPP) | wild-type | 37 |
| Age-associated cardiac dysfunction | atrial natriuretic factor | wild-type | 26 |
| Early-onset Alzheimer's disease | amyloid β-peptide | amyloid precursor protein (APP) and presenilin (PS1 & PS2) mutations | 40–43 |
| Early-onset Parkinson's disease | α-synuclein | A30P; A53T | 35 |
| Huntington's Disease | huntingtin | triplet repeat expansion | (Gln)$_{51}$–(Gln)$_{122}$ |
| Familial Creutzfeld-Jacob disease (fCJD) | PrP | | 27–30 |
| Fatal familial insomnia (FFI) | PrP | | 27–30 |
| Gerstmann-Straussler-Scheinker disease (GSS) | PrP | | 27–30 |
| Hereditary cerebral amyloid angiopathy | cystatin C | L68Q | 110 |
| Primary amyloidosis (systemic) | Ig light chain | | ~110 |
| Secondary amyloidosis (systemic) | serum amyloid A | | 74–87 |
| Familial amyloid polyneuropathy (FAP)-Portuguese- type | transthyretin | >40 mutations now identified | ≧81 |
| FAP (ApoA1 associated) | apolipoprotein A1 | R173P, | ~85 |
| FAP-Finnish type | gelsolin | D187N | 71 |
| Hereditary systemic amyloidosis | lysozyme | I56T, D67H | 71 |
| Prolactinoma of the pituitary | prolactin | | |
| Transferable Spongiform Encephalopathies | PrP | | 27–30 |

Formation of fibril structures is time-dependent for many of these proteins and their mutant forms. It is thought that oligomeric intermediates must form before fibril formation occurs. Blocking fibril formation will be useful in treating amyloid diseases, as will the ability to dissolve existing fibrils.

There is considerable disagreement as to the cytotoxic mechanism of Aβ: whether Aβ aggregates actually cause Alzheimer's disease, or whether the Aβ aggregates are merely an incidental result of the disease. Among researchers supporting the idea that Aβ aggregates cause Alzheimer's disease, there is further dispute as to whether it is the fibrils or the protofibrils that are the cause of the disease. Fibrils may be relatively inert or even cytoprotective, while the more active surface growth of the smaller protofibrils may cause cytotoxicity. More specifically, it has been proposed that it may be the exposed hydrophobic surfaces of the protofibrils that are cytotoxic. Recent results suggest that smaller Aβ aggregates are cytotoxic, while larger Aβ aggregates are inert or even cytoprotective. The weight of the evidence appears to support the hypothesis that it is the amyloid protofibrils (~1 nm×50 nm) that are in fact the toxic species underlying Alzheimer's disease.

M. Pallitto et al., "Recognition sequence design for peptidyl modulators of beta-amyloid aggregation and toxicity," *Biochemistry*, vol. 38, pp. 3570-3578 (1999) tested certain peptide-based inhibitors for cytoprotection of PC-12 cells in vitro. The putative "inhibitors" were reported actually to hasten aggregation of Aβ to higher molecular weight aggregates that were both more diffuse and more branched than normal fibrils.

There are a few in vitro models for amyloid disease. PC-12 rat neuronal cells have been used as an in vitro model for neuronal cell death from exposure to Aβ aggregates. The human IMR-32 neuroblastoma cell line has also been suggested as an in vitro model for Alzheimer's disease, but it has been relatively little used compared to PC-12 assays. See D. Neill et al., "Human IMR-32 neuroblastoma cells as a model cell line in Alzheimer's disease research," *J. Neurosci. Res.*, vol. 39, pp. 482-93 (1994).

Aβ aggregates cause a number of changes in PC-12 cells, including damage to normal mitochondrial processing. M. Pallitto et al., "Recognition sequence design for peptidyl modulators of β-amyloid aggregation and toxicity," *Biochem.*, vol. 38, pp. 3570-3578 (1999) reported that the diminished ability of PC-12 cells exposed to Aβ aggregates to reduce the fluorescence of 3-(4,5-dimethylthiazol-2-yl)-2,5-diphenyl-2,5-diphenyl-2H-tetrazolium bromide (MTT) could be used as an assay for cell damage. Their best inhibitors protected the PC-12 cells as measured by the effect on MTT assay. The peptide sequences KLVFF (SEQ ID NO: 1) and KLVF (SEQ ID NO: 2) were reported to provide a protective effect against Aβ toxicity. Peptides containing a lysine hexamer could sometimes act as a disruptive element.

Prior approaches to blocking amyloid aggregation have included the use of modified peptides based generally on a core domain of the native β amyloid protein, for example containing D-amino acids, or containing biotinylated groups. See, e.g., U.S. Pat. Nos. 5,854,204 and 6,277,826.

D. Wilcock et al., "Intracranially administered anti-Aβ antibodies reduce β-amyloid deposition by mechanisms both independent of and associated with microglial activation," *J. Neurosci.*, vol. 23, pp. 3745-3751 (2003) reported prior results that active vaccination with Aβ, and passive immunization with anti-Aβ antibodies both reduced levels of Aβ deposits in mice. This paper also reported the authors' results that intracranial injection of anti-Aβ antibodies in mice reduced Aβ plaques, through two different mechanisms: a faster mechanism not associated with microglial activity, and a slower mechanism associated with microglial activity.

FIGS. 1(a) and 1(b) (based in part on A. Lomakin et al., "On the Nucleation and Growth of Amyloid β-protein Fibrils: Detection of Nuclei and Quantitation of Rate Constants," *Proc. Natl. Acad. Sci. U.S.A.*, vol. 93, pp. 1125-1129 (1996)) depict two principal pathways for Aβ amyloid fibril initiation and growth, and depict how the equilibria of these pathways can be altered by the novel "blocker" peptides. When the concentration of Aβ is above the critical micelle concentration (~10-30 μM), as depicted in FIG. 1(a) the Aβ may form micelles (M). The micelles M rearrange into a protofibril P, which can grow and eventually aggregate to form a fibril F.

At lower, more physiologically relevant nM concentrations, M cannot form directly from Aβ, so growth occurs instead from an alternative initiator I, as shown in FIG. 1(b). Initiation in vivo is likely to involve cell surfaces, other proteins, and protein aggregates. The accumulation of Aβ onto I gives rise to a protofibrillar-like species P', which can then lead to fibril structures F'. The kinetics of the mechanisms shown in FIG. 1(b) are likely to differ substantially from those shown in FIG. 1(a), especially if I is on a surface such as a cell membrane. Blocker or inhibitor molecules might interact with each of these species. For example, to prevent fibrillogenesis (i.e., formation of F or F', but not necessarily M or P/P') a blocker molecule might interact specifically with P or P'. To dissolve already-formed fibrils, a blocker molecule could interact with F/F'to promote dissolution of Aβ from F/F'. In practice, the surfaces of M, P/P' and F/F' may be similar, presenting an extended peptide hydrogen-bonding edge and side-chain groups (either hydrophobic or hydrophilic, depending on the portion of Aβ targeted) for interaction with the blocker. By contrast, the initiators I may be unique, and thus may interact differently with different peptide inhibitors. Additionally, aggregation into β-sheet structures may be enhanced by chemical modification of the peptide by metabolites or by other compounds.

Structure of amyloid fibrils. The secondary structure of the amyloid fibrils associated with many of the diseases listed in Table 1, as determined by low resolution X-ray diffraction, including the fibrils associated with Alzheimer's disease, largely comprise β-sheets. Many researchers have assumed the amyloids to comprise primarily anti-parallel β-sheets connected by turn regions. More recently, however, higher resolution synchrotron X-ray diffraction studies have shown the amyloid fibril of mutant transthyretin to have quite a different structure, comprising primarily a β-sheet helix, in which a sequence of 24 β-sheet ribbons stack into a repeat of ~115 Å. Modeling suggests that two of these β-sheet helices pack via hydrophobic side-chain interactions. Two of these pairs fold into a structure in which two pairs of β-sheet helices (4 β-sheets total) twist about each other, analogous to what is seen in helical peptide coiled-coil structures. While this model says nothing explicitly about parallel versus anti-parallel construction of the β-sheet stacks, the diffraction patterns of the amyloid fibrils provide no experimental evidence for any anti-parallel stacking. The data could be explained by the absence of anti-parallel sheets (with only parallel sheets being present), or by the presence of a two-fold screw axis symmetry relating anti-parallel sheets, or by the presence of a mixture of anti-parallel and parallel sheets.

More support for parallel amyloid fibril β-sheets has recently been obtained from solid-state NMR spectroscopy using a $^{13}$C-labeled amino acid carbonyl near or within the hydrophobic aggregation-inducing sequence of Aβ$_{10-35}$, and using a DRAWS solid-state NMR experiment to determine the dipolar coupling between $^{13}$C atoms on adjacent peptide strands. Labeling of Gln$_{15}$, Lys$_{16}$, Leu$_{17}$, and Val$_{18}$ in different experiments has given inter-label distances of ~5 Å for all 4 peptides, indicating that in this region of the peptide the strands are oriented parallel to one another and are in registry. Neutron diffraction studies have further suggested that, in fact, the entire structure of Aβ$_{10-35}$ and the full length Aβ$_{1-40}$ in amyloid fibrils likely comprises parallel β-sheets.

Inhibition of Protofibril and Fibril Assembly as a Drug Target for Alzheimer's Disease.

There is growing evidence that the amyloid fibril itself is toxic in Alzheimer's and other amyloid-associated diseases, as well as evidence that a precursor aggregate, a protofibril or other smaller assembly of proteins, is also toxic. Targets for drug intervention in Alzheimer's disease include inhibiting the aggregation of amyloid β-protein (Aβ), as well as disassembly of protofibrils and fibrils of Aβ. Some groups have explored, for example, point mutations in the Aβ sequence.

Other strategies have included combinatorial approaches to screen short pentapeptides with L- or D-amino acids to develop small, mostly hydrophobic, inhibitors of Aβ$_{1-40}$ fibril formation. Some of these peptides themselves aggregate and form insoluble precipitates (e.g., Lys-Leu-Val-Phe-Phe) (SEQ ID NO: 1); and even the best of the peptides reported to date has required a tenfold molar excess to inhibit Aβ$_{1-40}$ fibril formation. Thus, these peptides can themselves become part of high order aggregates.

Another approach has been to incorporate a proline residue in the middle of a hydrophobic recognition sequence to inhibit β-sheet formation, as proline is not well accommodated in the middle of a β-sheet structure. This strategy can prevent self-aggregation of "blockers." Even short peptides in this series have been reported to inhibit fibril formation at a tenfold molar excess. The D-analogs of these peptides have also been reported to inhibit fibril formation. Coupling of putrescine (1,4-diaminobutane, PUT) to aspartate residues (or to the C-terminus) in these peptides produced molecules reported to have better ability to cross the blood-brain barrier, and to improve in vitro inhibition and bioactivity.

A different approach incorporates the recognition element (the hydrophobic aggregation-inducing sequence) in concert with a "disrupter" element (an oligolysine tail). Positioning the disrupter at the N-terminus leads to a highly self-aggregating peptide that is ineffective at inhibiting amyloid fibril formation, while addition of a disrupter unit at the C-terminus of the peptide produces a soluble peptide that inhibits fibril formation (as measured by thioflavin T assay), and that reduces the toxicity of Aβ in cell culture assays.

C. Toniolo et al., "Control of peptide conformation by the Thorpe-Ingold effect (C$^α$-tetrasubstitution)," *Biopolymers*, vol. 60, pp. 396-419 (2001, or 2002) reviews the conformational preferences of C$^α$-tetrasubstituted α-amino acids. The "Thorpe-Ingold" effect is the name given to the observation that C$^α$-tetrasubstitution tends to bring nearby atoms on both sides of the substituted carbon in close proximity.

U.S. Pat. No. 6,566,334 discloses the synthesis of certain C$^{α,α}$-disubstituted amino acids.

Presentations and publications from our research group (not admitted to be prior art), the complete disclosures of each of which is incorporated by reference, include the following: Y. Fu, "Facile Synthesis of Sterically Hindered α,α-Disubstituted Amino Acids and Their Incorporation into Peptides by Solid-Phase Peptide Synthesis, "Presentation at 222nd National Meeting of the American Chemical Society (Aug. 26, 2001); Y. Fu et al., "Sterically Hindered C$^{α,α}$-Disubstituted α-Amino Acids: Synthesis from α-Nitroacetate and Incorporation into Peptides," *J. Org. Chem.*, vol. 66, pp. 7118-7124 (2001); Y. Fu et al., "Efficient Acylation of the N-Terminus of Highly Hindered C$^{α,α}$-Disubstituted Amino Acids via Amino Acid Symmetrical Anhydrides," *Org. Lett.*, vol. 4, pp. 237-240 (2002); Y. Fu, "Artificial Peptides Containing C$^{α,α}$-Disubstituted Amino Acids: Synthesis, Conformational Studies, and Application as β-Strand Mimics," PhD Dissertation, Louisiana State University (Baton Rouge, La., submitted December 2002); J. Aucoin, "Determination of Possible Surface Adsorption of Beta-Amyloid Aggregate Species and Aggregation Inhibition Products Using Scanning Force Microscopy and Dynamic Light Scattering," Presentation at National Meeting of the American Chemical Society (Aug. 18, 2002); J. Aucoin et al., "Surface and Solution Studies of Beta-Amyloid Aggregation using Dynamic Light Scattering and Atomic Force Microscopy," Presentation at Pittsburgh Conference (Sep. 17, 2002); J. Aucoin, "Interplay between beta-Amyloid (1-40) and a Peptide-based beta-Amyloid Aggregation Inhibitor," presentation at 225th American Chemical Society conference (Mar. 23-27, 2003); and J. Aucoin, "Dissection of an Amyloid Aggregation Inhibitor," presentation at 225th American Chemical Society conference (Mar. 23-27, 2003). For example, the Fu PhD Dissertation at p. 126 discloses the peptide Dpg-Phe-Dbzg-Val-Dibg-(Lys)$_7$-NH$_2$ (SEQ ID NO: 18); and the fourth page of the Aucoin presentation from the 225th American Chemical Society conference discloses the peptide (Lys)$_6$-Dibg-Val-Dbzg-Phe-Dpg-Lys-NH$_2$ (SEQ ID NO: 19).

Design and Synthesis of New β-Strand Mimics to Block Amyloid Fibril and Protofibril Formation.

We have discovered novel peptides that may be used as inhibitors of amyloidogenesis, as suppressors of amyloid toxicity, and as therapeutic agents for amyloid-associated diseases. These new β-strand mimics (β-sheet "blockers") specifically interact with and block the development of the β-sheet structure of the developing fibrils of amyloid diseases, such as Alzheimer's disease amyloid β-peptide (Aβ). We have discovered that oligomerization of β-sheet structures, including those implicated in amyloid-associated diseases such as Alzheimer's disease, Parkinson's disease, Huntington's disease, type II diabetes, and the other diseases listed in Table I, may be inhibited or even reversed by the presence of extended peptide structures that have only one edge available for hydrogen bonding. Without a second edge that is also available for hydrogen bonding, the extension of a developing β-sheet is blocked by binding to the novel peptides. Embodiments of the novel β-strand mimics/blockers include peptides having alternating natural L-amino acids and C$^{α,α}$-disubstituted amino acids (ααAAs) whose side-chains are larger than methyl (e.g., ethyl, propyl, isopropyl, isobutyl, benzyl, etc.). Such ααAAs with bulky side chains favor extended conformations. These structures will only form hydrogen bonds from one edge of the β-strand, as one face is blocked by the pro-R alkyl groups of the ααAAs. Thus extension of the β-sheet is blocked. See generally C. Toliolo et al. (2002).

BRIEF DESCRIPTION OF THE DRAWINGS

FIGS. 2(a) through 2(c) depict examples of amino acids and peptides that may be used in the present invention. FIG. 2(a) depicts a "standard" α-amino acid with a single side chain R. FIG. 2(b) depicts a $C^{\alpha,\alpha}$-disubstituted amino acid with two side chains, $R_S$ and $R_R$. The $R_S$ and $R_R$ groups may for example, include propyl, isopropyl, butyl, isobutyl, benzyl, or other functional groups—particularly including, but not limited to, two occurrences (rather than just one) of the same side chains that occur in the corresponding natural amino acids in an aggregation-inducing sequence of an amyloid protein. Although the $R_S$ and $R_R$ groups may be the same or different, as a practical matter it will usually be easier to synthesize achiral $C^{\alpha,\alpha}$-disubstituted amino acids in which the $R_S$ and $R_R$ groups are both the same. FIG. 2(c) depicts an embodiment of the novel blocker peptides containing a $C^{\alpha,\alpha}$-disubstituted amino acid. Note that there is a hydrogen-bonding edge available for hydrogen-bonding to a protofibril or fibril, and a blocked edge where the substituents on the amino acids block further hydrogen bonding on that edge.

Figure 1A:
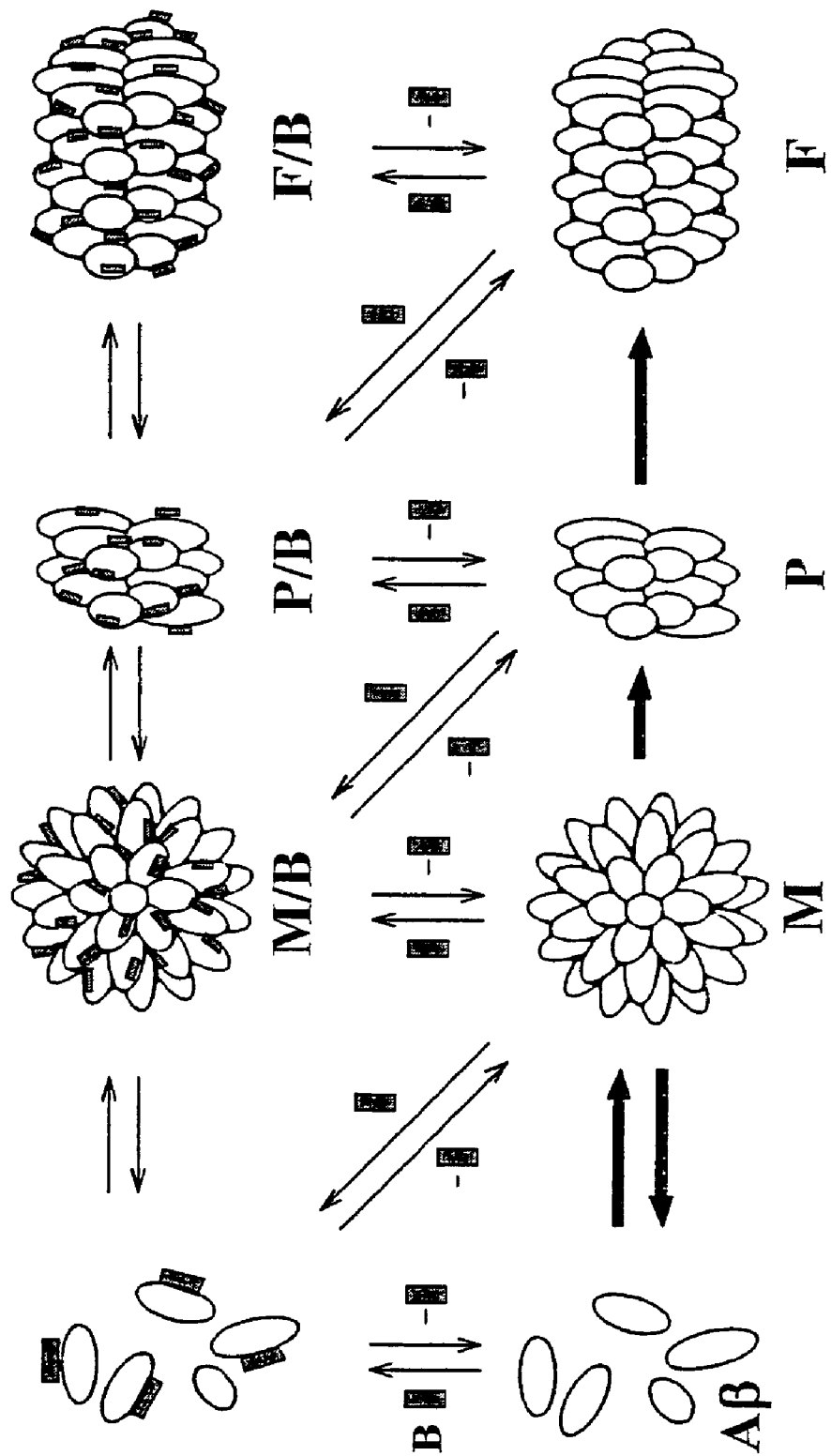
FIGS. 1(a) and 1(b) depict two principal pathways for Aβ amyloid fibril initiation and growth, and depict how the equilibria of these pathways can be altered by the novel "blocker" peptides.
Figure 1B:
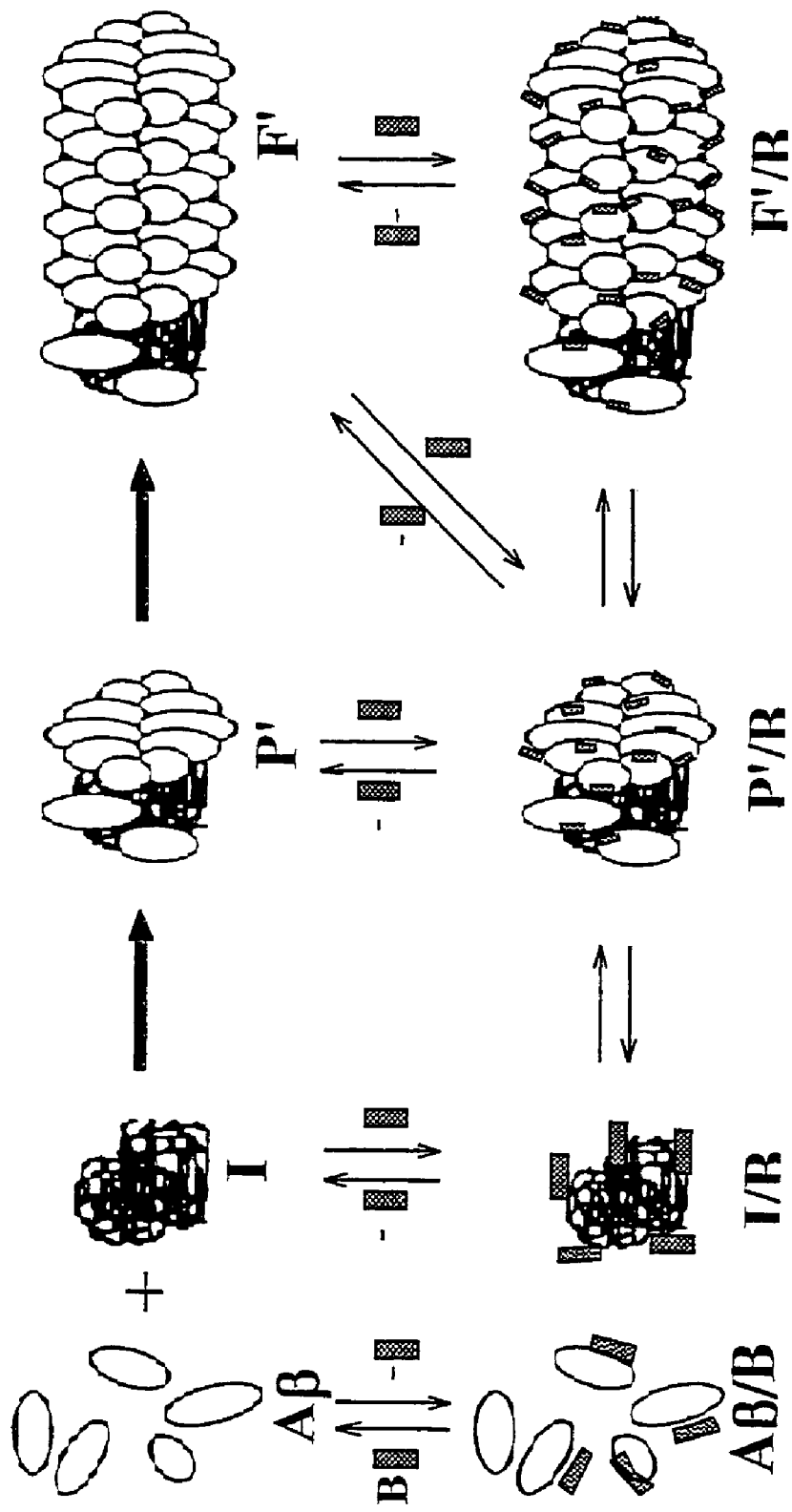
Figure 2A:
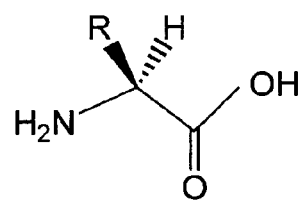
FIGS. 2(a) through 2(c) depict amino acids and peptides that may be used in the present invention.
Figure 2B:
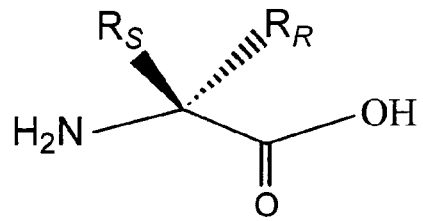
Figure 2C:
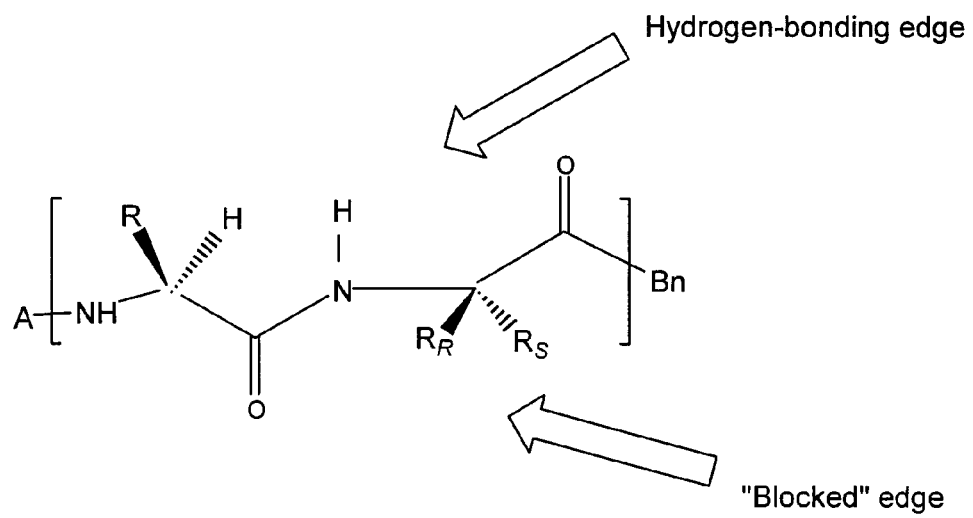

β-Strand mimics in accordance with the present invention include, for example, peptides having the following formulas, or compounds including peptidyl sequences having the following formulas:

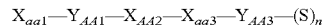

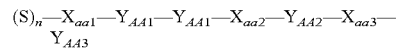

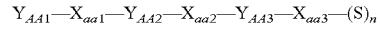

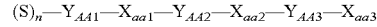

wherein:

(a) The amino acids $X_{aa1}$, $X_{aa2}$, and $X_{aa3}$ are either the same as, or are homologous to, alternating amino acids found in a hydrophobic aggregation-inducing sequence of an amyloid-forming protein, and have side chains adapted for cross-strand side chain interactions with a β-sheet. The amino acids $X_{aa1}$, $X_{aa2}$, and $X_{aa3}$ are based on alternating amino acids in the native protein, since the compositions are intended to inhibit or otherwise influence β-sheets, and in a β-sheet conformation alternating amino acids are found on the same face. Thus, for example, in the β-amyloid hydrophobic aggregation-inducing sequence Aβ$_{16-21}$ (KLVFFA) (SEQ ID NO: 3), the "alternating" amino acids are K-V-F or L-F-A. Thus $X_{aa1}$, $X_{aa2}$, and $X_{aa3}$ might be K, V, and F, respectively, or they might be L, F, and A, respectively. Note that the amino acids need not be identical to the corresponding native amino acids. They might, for example, instead be D-conformation amino acids. Or other hydrophobic amino acids of similar size and shape might be substituted for a hydrophobic amino acid. Such substituted amino acids might be naturally occurring amino acids or synthetic amino acids, such as are known in the art. For example, L might be replaced with I or V, F might be replaced with Y or W, A might be replaced with V, and V might be replaced with A. In the case of a hydrophilic amino acid, another hydrophilic amino acid might be substituted: D-form or L-form, natural or synthetic, acidic or basic. For example, K might be replaced with R, H, D, E, T, or S.

(b) At least 1, preferably 2, and more preferably all 3 of the amino acids $Y_{AA1}$, $Y_{AA2}$, and $Y_{AA3}$ are $C^{\alpha,\alpha}$-disubstituted amino acids with side chains that do not readily hydrogen bond. Any of the $Y_{AA1}$, $Y_{AA2}$, and $Y_{AA3}$ that are not $C^{\alpha,\alpha}$-disubstituted amino acids may instead be other amino acids. In each case, the $Y_{AA1}$, $Y_{AA2}$, and $Y_{AA3}$ should preferably be chosen to have the same general side chain properties (e.g., size, charge, polarity) as occur in the natural protein, to promote β-sheet stability. The $Y_{AA1}$, $Y_{AA2}$, and $Y_{AA3}$ amino acids will preferably correspond (in this general manner) to the amino acids in the natural protein on either side of those corresponding to the $X_{aa1}$, $X_{aa2}$, and $X_{aa3}$ amino acids. For example, referring again to the β-amyloid hydrophobic aggregation-inducing sequence Aβ$_{16-21}$ (KLVFFA) (SEQ ID NO: 3), if $X_{aa1}$, $X_{aa2}$, and $X_{aa3}$ are chosen to be K, V, and F, respectively, then $Y_{AA1}$, $Y_{AA2}$, and $Y_{AA3}$ should correspond in this general manner to L, F, and A. For example, $Y_{AA1}$, $Y_{AA2}$, and $Y_{AA3}$ might be Dibg ($C^{\alpha,\alpha}$-diisobutylglycine); Dbzg ($C^{\alpha,\alpha}$-dibenzylglycine); and Dpg ($C^{\alpha,\alpha}$-dipropylglycine), respectively. ($Y_{AA3}$ in this example is Dpg, rather than $C^{\alpha,\alpha}$-dimethylglycine, also known as Aib, because the latter is known to favor a helical conformation, while the former favors an extended β-sheet conformation. Aib has not yet been tested in the present invention, but it may also be useful despite its tendency to favor a helical conformation.) Preserving the same general side chain properties (e.g., size, charge, polarity) helps promote the stability of a β-sheet into which the novel peptides are incorporated, based on the principle that "like likes like." Note that the $C^{\alpha,\alpha}$-disubstituted amino acids may be either chiral or achiral, but as a practical matter the achiral amino acids will usually be less burdensome to synthesize and purify.

(c) $(S)_n$ denotes a stretch of (generally) water soluble (hydrophilic) amino acids or other functionalities. The number of groups n is preferably between 0 and about 10, most preferably about 4-6. These groups may, for example, include polar or charged amino acids or other moieties having amino functionality, carboxy functionality, hydroxy functionality, and the like. These groups may, for example, include polyethylene glycol, oligo (ethylene glycol), oligo-lysine, oligo-arginine, oligo-histidine, oligo-aspartic acid, oligo-glutamic acid, various mixtures of these functionalities, and the like.

(d) Although not expressly depicted in the formulas shown above, the amino-terminus, the carboxy-terminus, or both of the β-strand mimics may include other functionality that would not interfere with the intended use of the peptides. For example, the C-terminus may be carboxy or amide or N-alkylated amide, the N-terminus may be amino or amide or blocked with acetyl or another group, and the like.

The number of amino acids in the aggregation-inducing sequence need not be the same as the number of amino acids in the blocking peptidyl sequence. While the sequences shown above are based on at least six amino acids, sequences formed according to the same pattern but having at least four or five amino acids in such a pattern are also within the contemplation of the present invention.

The peptides (or peptide-containing compounds) adopt an extended backbone structure due to the conformational preference of the bulky ααAAs; and they interact with amyloid strands based on a "like likes like" residue relationship. The presence of ααAAs at alternating sequence positions allows hydrogen bonding on one side of the β-strand mimics, while blocking further addition from the opposite side. The water soluble group $(S)_n$ at either the N-terminus or the C-terminus inhibits elongation of the amyloid β-structures, and also increases the inhibitor's solubility in aqueous solution.

Figure 3:
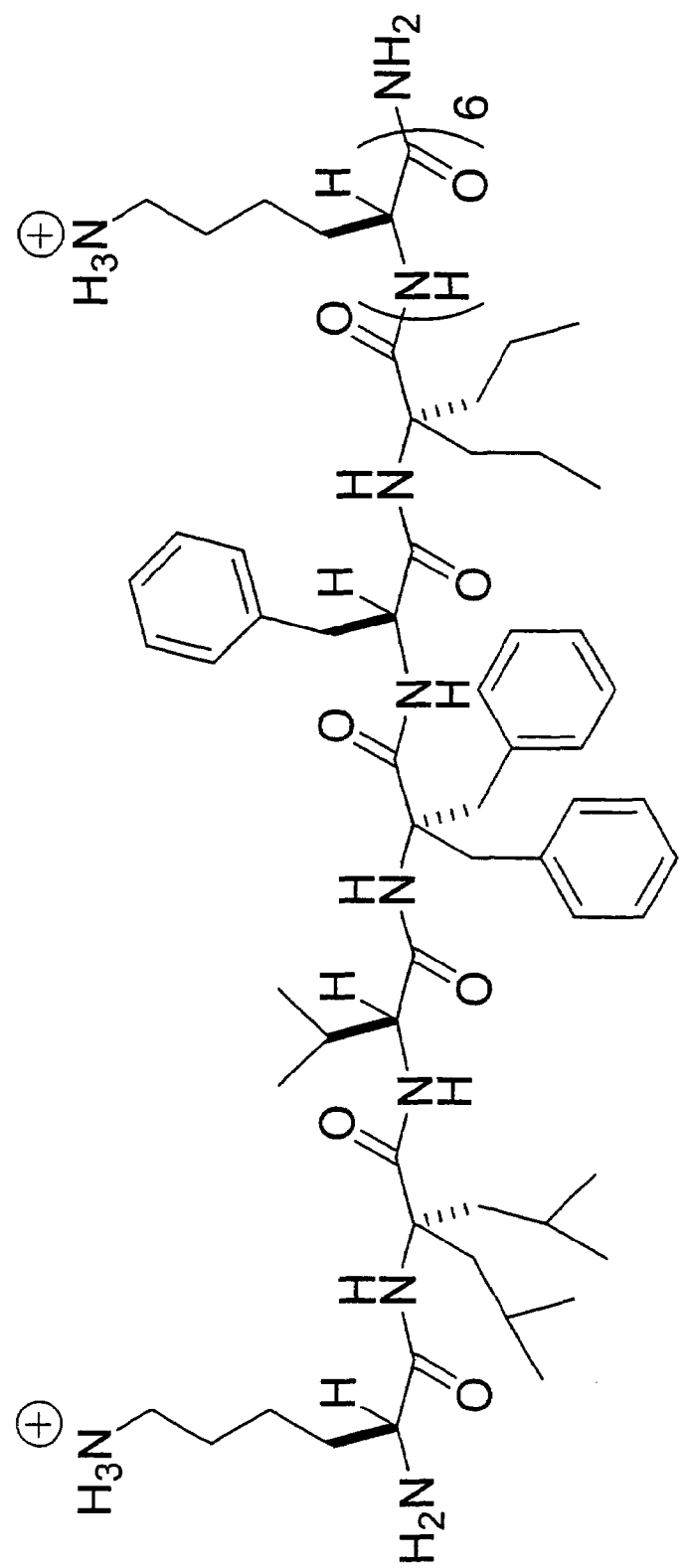
FIG. 3. depicts the blocker peptide AMY-1.
Figure 4:
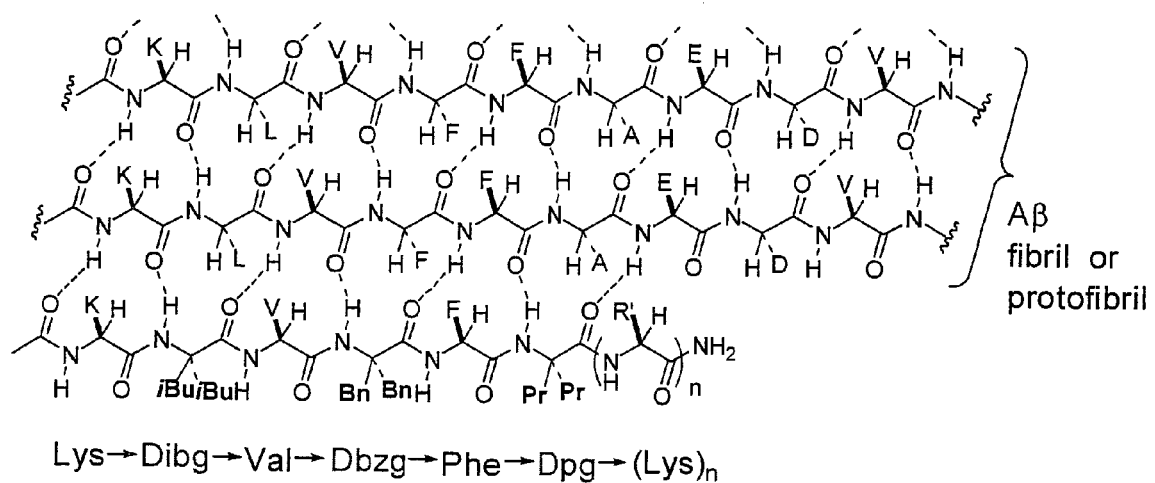
FIG. 4 depicts the manner in which AMY-1 blocks further extension of a growing β-sheet formed from the Aβ peptide.
Figure 5A:
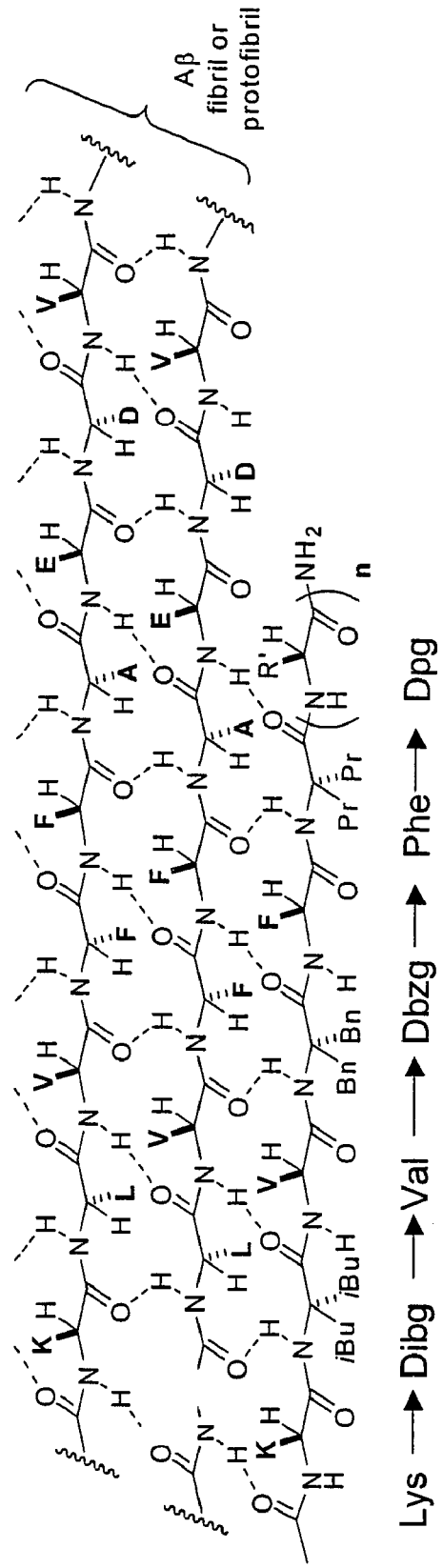
FIGS. 5(a)-(d) depict examples of both parallel and anti-parallel constructs, showing interactions of fibrils with the blocker peptides.
Figure 5B:
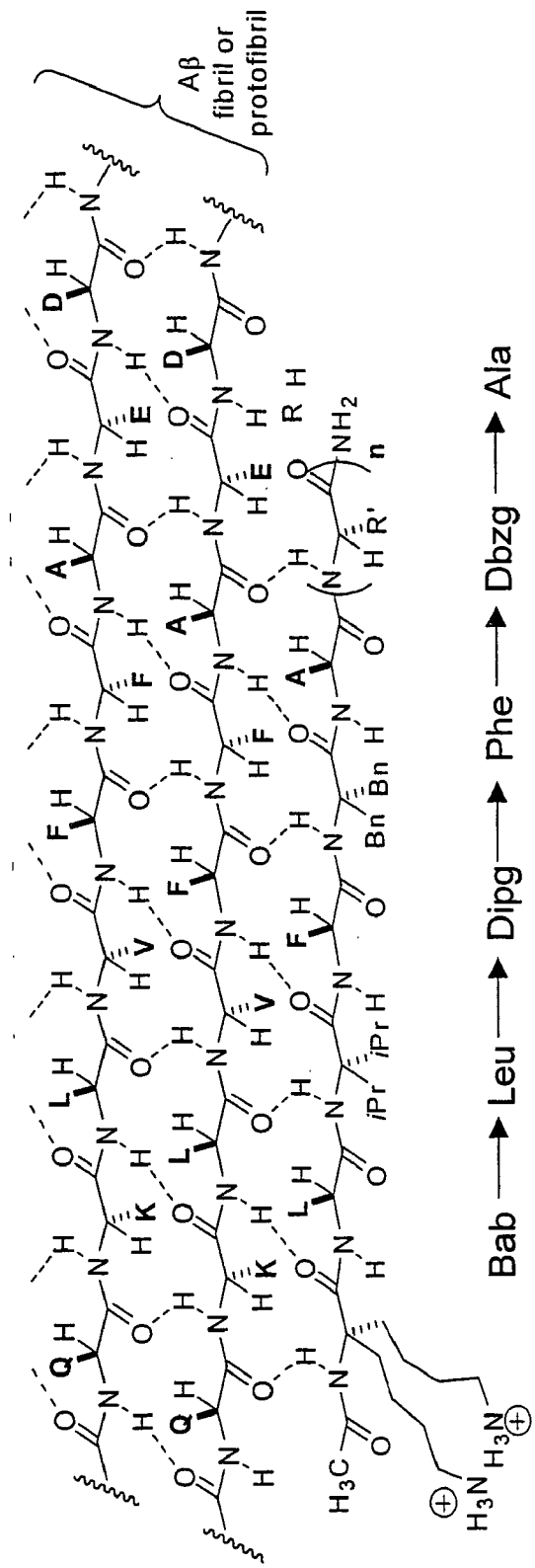
Figure 5C:
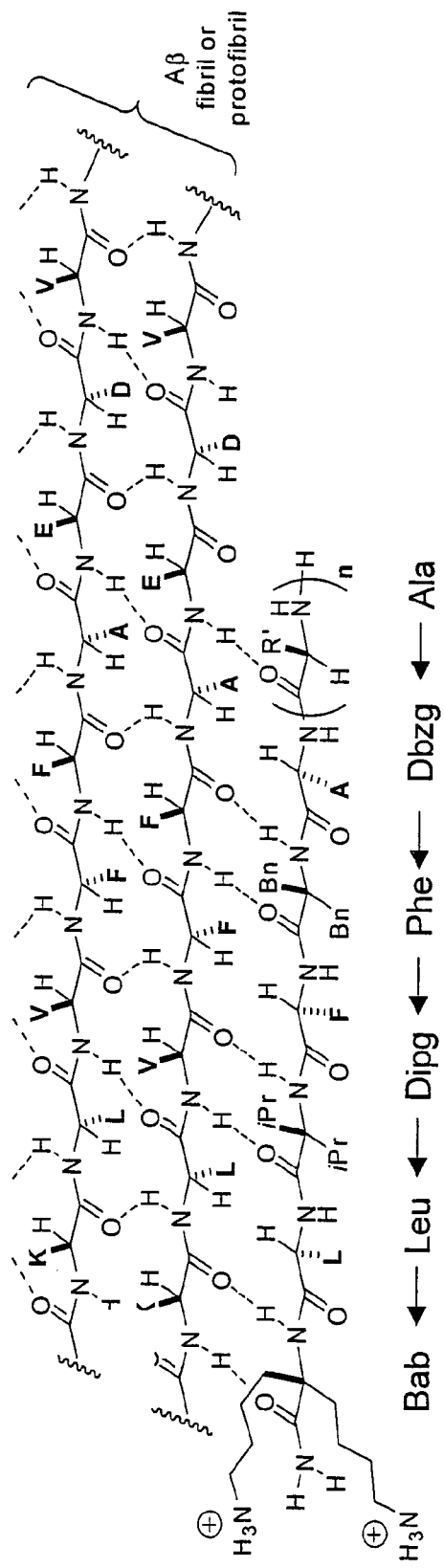
Figure 5D:
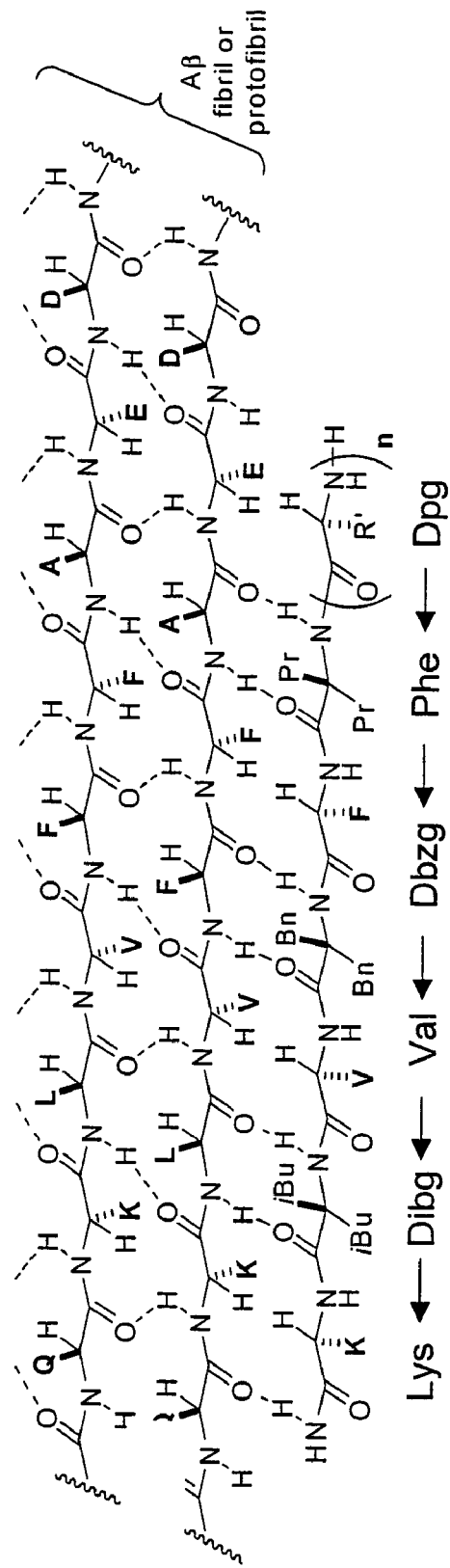

For example, one embodiment of a blocking β-strand mimic that we have synthesized, based on the β-amyloid hydrophobic aggregation-inducing sequence $A\beta_{16-21}$ (KLVFFA) (SEQ ID NO: 3), is the following:

Lys-Dibg-Val-Dbzg-Phe-Dpg- (AMY-1) (SEQ ID NO: 4)
$(Lys)_6$-$NH_2$ wherein Dibg is $C^{\alpha,\alpha}$-diisobutylglycine; Dbzg is $C^{\alpha,\alpha}$-dibenzylglycine; and Dpg is $C^{\alpha,\alpha}$-dipropylglycine. The AMY-1 peptide inhibits aggregation at concentrations of ~5 μM when incubated with the amyloidogenic peptide $A\beta_{10-35}$ in phosphate buffer at 37° C., under conditions where the $A\beta_{10-35}$ peptide alone would form amyloid fibrils. Also, the AMY-1 peptide does not aggregate with itself, and it may assist in disaggregating existing amyloid fibrils. AMY-1 is also depicted in FIG. 3. FIG. 4 depicts the manner in which AMY-1 blocks further extension of a growing β-sheet formed from the Aβ peptide.

Other embodiments of the blocking β-strand mimics that we have synthesized, based on the β-amyloid hydrophobic aggregation-inducing sequence $A\beta_{16-21}$ (KLVFFA) (SEQ ID NO: 3), include the following:

$(Lys)_7$-Dibg-Val-Dbzg-Phe- (AMY-2) (SEQ ID NO: 5)
Dpg-$NH_2$

Lys-Dibg-Val-Dbzg-Phe-Dpg- (AMY-3) (SEQ ID NO: 7)
$NH_2$

Lys-Dibg-Val-Dbzg-Phe-Dpg- (AMY-4) (SEQ ID NO: 6)
Lys-$NH_2$

Lys-Dibg-Val-Dbzg-Phe-Lys- (AMY-5) (SEQ ID NO: 17)
$NH_2$

Some preliminary studies have produced results that support the following conclusions (data not shown): (1) The interaction between AMY-1 and $A\beta_{1-40}$ produces a small, non-fibril aggregate—even after a 4.5 month-incubation, no massive fibrils were formed. (2) The interaction between AMY-2 and $A\beta_{1-40}$ rapidly produces a large, non-fibril aggregate. (3) AMY-2 self-aggregates at 50 μM.

In general, compounds designed to inhibit the fibrils or protofibrils, or to inhibit the toxicity of fibrils or protofibrils of amyloid-associated proteins may differ from one amyloid disease to another, based on differences in the aggregation-inducing sequences of the respective amyloid-associated proteins. As discussed above, the amino acids of the blocker compounds generally correspond to the aggregation-inducing sequence of the target amyloid-associated protein, meaning that the amino acids are either the same as those of a sequence within the aggregation-inducing sequence, or they are generally homologous in terms of side chain size and hydrophobicity. One set of alternating amino acids is the same as the corresponding native amino acids, or comprises natural or synthetic amino acids generally homologous in terms of size and hydrophobicity. The other set of alternating amino acids, those that are on the opposite face in a β-sheet conformation, comprise at least some, if not all, $C^{\alpha,\alpha}$-disubstituted amino acids. Examples of aggregation-inducing sequences for amyloid diseases, sequences that may be targeted through compounds in accordance with the present invention, include those shown in Table 2.

TABLE 2

| Protein | Core Aggregation-inducing sequence(s) | Reference |
| --- | --- | --- |
| Amylin (IAPP) | FLVHS (SEQ ID NO: 9) NFLVH (SEQ ID NO: 10) | Y. Mazor et al., "Identification and characterization of a novel molecular-recognition and self-assembly domain within the islet amyloid polypeptide, J. Mol. Biol., vol. 322, pp. 1013-1024 (October 2002) |
| Amylin (IAPP) | LANFLV (SEQ ID NO: 14) FLVHSS (SEQ ID NO: 15) | L. A. Scrocchi et al., "Identification of minimal peptide sequences in the (8-20) domain of human islet amyloid polypeptide involved in fibrillogenesis," J. Structural Biol., vol. 141, pp. 218-227 (2003) |
| Amylin (IAPP) | NFGAIL (SEQ ID NO: 11) | A. Kapurniotu et al., "Structure-based design and study of non-amyloidogenic, double N-methylated IAPP amyloid core sequences as inhibitors of IAPP amyloid formation and cyto-toxicity, J. Mol. Biol., vol. 315 (January 2002) |
| Fibrinogen | AGDV (SEQ ID NO: 16) | N. Podolnikova et al., "Identification of a novel binding site for platelet integrins $\alpha_{IIb}\beta_3$ (GPIIbIIIa) and $\alpha_5\beta_1$ in the γC-domain of fibrinogen," J. Biol. Chem., vol. 278, pp. 32251-32258 (2003) |
| Gelsolin | (see text of reference) | Amyloid J. Protein Folding Disorders, vol. 9, pp. 75-82 (2002) |
| Synuclein | VGGAVVTGV (SEQ ID NO: 12) GAV | H. Du et al., "A peptide motif consisting of glycine, alanine, and valine is required for the fibrillization and cyto-toxicity of human alpha-synuclein, Biochem., vol. 42, pp. 8870-8878 (July 2003) |

TABLE 2-continued

| Protein | Core Aggregation-inducing sequence(s) | Reference |
|---|---|---|
| PrP | PrP(180-193): VNITIKQHTVTTTT (SEQ ID NO: 13) | D. Grasso et al., "Interaction of prion peptide PrP 180-193 with DPPC model membranes: a thermodynamic study," New J. Chem., vol. 27, pp. 359-364 (2003) |
| Huntington's Disease | $(Gln)_m$ m is from ~25 to ~45 | J. Morley et al., "The threshold for polyglutamine-expansion protein aggregation and cellular toxicity is dynamic and influenced by aging in *Caenorhabditis elegans*," Proc. Natl. Acad. Sci. USA, vol. 99, pp. 10417-10422 (August 2002) |

Some familial forms of amyloid diseases (see, e.g., examples in Table 1) appear to be caused by the increased aggregation propensity resulting from a point mutation in the associated protein. Where the precise location of the aggregation-inducing sequence may not be known, one may still generate blocker peptides molecules by preparing peptides based upon an amino acid sequence at and around the location of the point mutation. For example, early onset Parkinson's disease may be caused by several mutations in alpha-synuclein, including Ala→Pro at position 30 (A30P) and Ala→Thr at position 53 (A53T). Blocker peptides based upon the sequences around the locations of such point mutations may also be effective inhibitors of amyloid aggregation.

Also, inhibition of amyloid protein aggregation by blocker peptides may be carried out by interactions of other portions of the amyloid protein that are involved in the interactions leading to assembly of the protein into repetitive β-sheets.

We have also discovered the surprising result that at least some of these compounds, for example the peptide AMY-2, may not inhibit amyloid aggregation at all, but instead may cause aggregation into a non-toxic, non-fibril conformation.

Without wishing to be bound by this theory, we hypothesize that toxicity may result from the interaction of protofibrils, and therefore that reducing the available concentration of protofibrils—not just of fibrils—will be significant clinically.

We have also discovered an efficient synthesis for peptides containing highly hindered ααAAs at internal positions. In one embodiment, the N-terminus of Dbzg or Dibg is readily acylated by amino acid symmetrical anhydrides in the absence of base. By contrast, acylation using conventional coupling techniques does not give good yields. Coupling with symmetrical anhydrides may be carried out in a non-polar solvent, with activity enhanced by anchimeric assistance from intermolecular hydrogen bonding between the NH of ααAAs and the carbonyl oxygen of the anhydrides. The symmetrical anhydride synthesis provides superior results. See Y. Fu et al., "Efficient Acylation of the N-Terminus of Highly Hindered $C^{\alpha,\alpha}$-Disubstituted Amino Acids via Amino Acid Symmetrical Anhydrides," *Org. Lett.*, vol. 4, pp. 237-240 (2002).

β-Sheets and "Blocker" Design

The β-sheet is one of three major secondary structures found in peptides and proteins. When there are two or more individual strands making up a β-sheet, those strands can be parallel or antiparallel relative to one another. The dimers have two distinctly different α-carbon environments. We define the "endo" α-hydrogens as being those on the inside of two given strands in a β-sheet conformation, and the "exo" α-hydrogens as being those on the outside. Steric interactions of the endo α-H's cause the sheet to pleat. Thus replacing the endo α-H's with a large group would tend to inhibit sheet formation. On the other hand, replacing the exo α-H's would not prevent dimerization, but would inhibit the addition of another extended peptide to the sheet. In one strategy (e.g., Compound 1), we replace alternate α-H's with alkyl groups to inhibit the addition of further sheets to a growing peptide, while still allowing hydrogen bonding on the opposite edge. Additionally, ααAAs having side chain groups larger than methyl favor an extended ("$C_5$") peptide conformation.

Substituents larger than methyl in the exo pro-R position are likely to stabilize individual strand extended conformations. Also, the presence of a substituent larger than a proton in the exo pro-R position will inhibit exo hydrogen-bond-mediated oligomerization. Thus, one embodiment of the invention uses peptides with alternating α-amino acids and ααAAs, the latter of which have substituents larger than methyl groups: e.g., dipropylglycine (Dpg), dibenzylglycine (Dbg), diiso-butylglycine (Dibg), diisopropylglycine (Dipg) or bis(aminobutyl)glycine (Bab). These amino acids are achiral analogs of the L-amino acids found in the $A\beta_{16-20}$ aggregation-inducing sequence.

An alternative approach to block one face of an extended peptide from forming a further β-sheet structure is to replace exo amide hydrogens with alkyl groups.

Examples of both parallel and anti-parallel constructs for these two approaches are depicted in FIGS. 5(a)-(d), showing the blocker peptides interacting in a "like-likes-like" in-registry with amyloid (depicted as two parallel strands). As shown in FIGS. 5(a)-(d), there are two possible registries (I and II). Thus for each class of peptide, there are four possible in-registry interactions with a growing fibril. In addition to acting as blockers, derivatives of the novel compounds may also be prepared with solubilizing groups or "disruptors" (e.g., oligo-lysine, oligoglutamate) at either end or both ends of the molecule. The effects of such disruptors on the kinetics of fibril formation may vary on different types of surfaces—e.g., hydrophobic, polar (hydrogen bonding), or charged (anionic or cationic) surfaces.

An alternative embodiment is a variation of Compound 1 using chiral ααAAs with charged groups in the exo pro-R position of the blockers. Charged or polar groups can also be incorporated "in plane." The charged or polar functionality can enhance solubility of Aβ, thereby modulating bioactivity, bioavailability, or both.

The embodiments in which alternating α-amino acids are ααAAs produce individual strands with a significant preference for an extended conformation. Structures may be elucidated, for example, from concentration-dependent CD spectra similar to those seen for α-helical peptides forming coiled-coil dimers. At a sufficient length, but at low concentrations, the individual strands should have CD spectra indicating a mixture of random coil and β-sheet conformations, becoming predominantly β-sheet as the peptide concentration increases.

Our intermolecular β-sheet dimer models allow homodimerization as well as heterodimerization between strands with complementary side chain interactions (e.g., with Aβ). While we do not expect to observe much self-aggregation of Compound 1 because of lack of side-chain complementarity, others may self-aggregate. One option to inhibit self-aggregation is to add charged groups on the ends of blockers. Previous studies of β-sheet-containing proteins and β-sheet models have suggested that side-chain/side-chain interactions across the strand, either hydrophobic interactions or salt bridges, are at least as important as "edge" complementary hydrogen bonding in stabilizing the β-sheet structure. Thus, we expect our inhibitors to be specific for interactions with Aβ or growing aggregates of Aβ because of the specific side chain interactions built into the design.

We expect the novel inhibitors to be resistant to protease degradation because of their highly modified nature, without the need to incorporate D-amino acids. For example, preliminary studies in our laboratory with peptides containing more than 40% ααAAs have shown high stability to trypsin digestion (data not shown). Thus these compounds should have high biostability, have high bioavailability, and should be well-suited for oral administration. See U.S. Pat. No. 6,566,334.

In addition to treating Alzheimer's disease, the novel approach may be used in treating other amyloid diseases, such as some of the systemic amyloidoses, various forms of FAP, age-associated type II diabetes, and other diseases listed in Table 1. The prion diseases share with Alzheimer's disease the formation of insoluble β-sheet structures that may also be inhibited by complementary extended peptide analogs. In addition, peptide analogs that favor an extended conformation are promising, as they may be generalized to inhibit other protein-protein interactions mediated by β-sheet interactions.

Inhibition Mechanism of Protofibrillogenesis with β-Strand Mimics: Capping, Dissolution, or Both.

Assays for large fibril formation (e.g. turbidity, Congo Red staining, thioflavine-T fluorescence) have previously been used to judge the effectiveness of fibrillogenesis inhibitors. However, testing for protofibril inhibition is new. One method to assay for protofibril inhibition combines microscopy and solution-based measurements. To confirm that potentially toxic protofibril formation is inhibited or reversed by "blocker" molecules, we employ scanning force microscopy (SFM) to observe the formation and dissolution of β-amyloid protofibrils, both in the presence and absence of molecules that inhibit fibril formation. SFM observations may be augmented by one or more solution methods, including techniques such as analytical ultracentrifugation (AU), dynamic light scattering (DLS), static light scattering (SLS), and fluorescence photobleaching recovery (FPR). The effects of other fibril-inhibiting molecules, in addition to the novel inhibitors, are also observed for comparison.

There have been some previous small, mainly hydrophobic peptides that block fibrillogenesis simply by capping the growing amyloid sheets. By comparison, without wishing to be bound by this theory, it is believed that the hydrophobic aggregation-inducing sequence of the novel peptides (and perhaps other hydrophilic groups) may be able both to block and to dissolve amyloid fibrils or protofibrils. Alternately, it is possible that the novel blocker molecules may or may not decrease rates of amyloid formation, but that they would change the aggregate morphology in a way that reduces toxicity of the fibrils.

Effect of Blocker Peptide on Large Fibril Seeds, and on Aβ Residence Time in Large Fibrils.

An effective therapeutic agent should function in an environment that already contains Aβ fibrils. Protofibrils rapidly assemble into fibrils if they are "seeded" with even a small concentration of large fibrils. The large fibrils compete for the same sites as do the blocker peptides. Analysis of results is complex. For example, a mixture of Aβ monomer, small aggregates, protofibrils, large fibrils, and blocker peptides would be difficult to study by either SLS or DLS, due to the low selectivity of these otherwise powerful methods. Furthermore, it is difficult to detect small particles in the presence of larger ones by scattering techniques. Analytical centrifugation tends to sediment the large fibril seeds, isolating them from the protofibrils and smaller components. The FPR method we will employ should have high selectivity, however. Similar to fluorescence correlation spectroscopy, one sees only what has been labeled, and practically any liquid-phase diffusion coefficient can be measured. FPR also operates well in moderately turbid solutions and is relatively "forgiving" in regard to fluorophore concentration. A large number of fluorophores contributes to a "quiet" signal having a simple exponential form that yields an absolute diffusion coefficient without the need for calibration. These characteristics allow observation of the fate of small Aβ molecules in the presence of blocker, fibril, or both. The lifetime of Aβ monomer may thus be measured in the presence of fibrils, with or without blocker peptide.

Fibrillogenesis on Hydrophobic and Hydrophilic Surfaces.

The nM concentration of extracellular Aβ in cerebral spinal fluid and other tissues is well below the approximately 30 μM concentration that has previously been reported as a minimum for initiating fibril formation in vitro. Without wishing to be bound by this theory, we hypothesize that the in vivo formation of Aβ protofibrils and fibrils results from interactions between soluble Aβ and various moieties on the surfaces of neurons. Without wishing to be bound by this theory, we believe that such "surface-induced" or "surface-nucleated" Aβ polymerization can be stopped or even reversed by the presence of the novel β-strand mimics. We will confirm these two hypotheses with ex situ and in situ scanning force microscopy (SFM).

Blocker Peptide Cytoprotection of Neuronal Cells from Aβ Aggregates; Correlation of Aβ Aggregate Size with Cytotoxicity.

The PC-12 rat neuronal cell line is a well-established in vitro model for Alzheimer's disease. Varying concentrations of characterized fibrils and protofibrils are tested for cytotoxicity against PC-12 cells. Then the cytoprotective activity of the blocker peptides against the cytotoxic fibrils and protofibrils is tested. Without wishing to be bound by this theory, we hypothesize that blocker peptides will exhibit cytoprotective activity by either of two mechanisms. The blocker peptides may break up and redissolve fibrils and protofibrils; or they may actually increase the rate of fibril formation, but by forming alternative, non-toxic Aβ aggregates. The assay will correlate Aβ aggregate size directly with fibril and protofibril concentrations, as well as possible surface-initiated Aβ aggregates.

Dissolution of Fibrils

Preliminary experiments have confirmed that the novel peptides can promote the dissolution of existing fibrils. The ability of the peptide AMY-1 to dissolve preformed fibrils was assessed with both scanning probe microscopy (SPM) and transmission electron microscopy (TEM). An image created by SPM at 10×10 μm² (not shown) indicated the presence of less adsorbed Aβ protein on mica in the presence of AMY-1. In the absence of AMY-1, another image made under otherwise similar conditions revealed bundles of fibrils and smaller aggregated materials. As seen with TEM, preformed β-amyloid in the absence of AMY-1 displayed numerous fibrils and annular fibrils, while in the presence of AMY-1, the fibrillar structures were substantially frayed. A twisting appeared in the middle of the length of the fibril, as if the AMY-1 peptide was interpolating into it.

In Vivo Testing in Mice

There are several transgenic mouse models of Alzheimer's disease. In some of these models the mice overexpress either the amyloid precursor protein (APP) or associated processing enzymes, thereby increasing the concentration of β-amyloid or producing a higher concentration of a more aggregation-prone β-amyloid subtype (the 42-residue isoform). These mice experience very early formation of β-amyloid plaques in the brain, and can be used to study compounds that prevent or disaggregate β-amyloid fibrils. Following the methods of D. Wilcock et al. (2003), we will directly inject inhibitor molecules into the hippocampus of APP transgenic mice, and then observe clearance of β-amyloid fibrils from the brain by immunohistochemistry and chemical staining techniques. Additionally, microglial cell activation will be observed to determine whether the injection of blocker molecules activates of the immune system. It is expected that the blocker peptides will induce fairly rapid clearing of fibrillic and other β-amyloid aggregates from the infused areas, with minimal associated necrosis.

Design and Synthesis of New β-Strand Mimics for Blocking Amyloid Fibril and Protofibril Formation.

Synthesis of Protected ααAAs for Incorporation into Fibrillogenesis Inhibitors

The procedure of C. Wysong et al., "4-Aminopiperidine-4-carboxylic acid: A cyclic alpha, alpha-disubstitued amino acid for preparation of water-soluble highly helical peptides," *J. Org. Chem.*, vol. 61, pp. 7650-7651 (1996); and of U.S. Pat. No. 6,566,334 was used to prepare ααAAs with hydrophobic side-chains. This procedure gives high yields of the crystalline hydantoins, which are then hydrolyzed in strong base at high temperature to produce the free amino acids. We have found the silylation/Fmoc procedure of D. Bolin et al., "Preparation of oligomer-free N-alpha-Fmoc and N-alpha-urethane amino acids," *Int. J. Pept. Protein Res.*, vol. 33, pp. 353-359 (1989), to give better yields and easier purification of the Fmoc-protected amino acids. All the hydantoins have been made and the Fmoc-Dpg-OH and Fmoc-Dibg-OH have been prepared with good yields. The dibenzylhydantoin and diisopropylhydantoin cleave more slowly, giving lower yields of the free amino acids.

Interaction of β-Amyloid and AMY-2

The interaction of β-Amyloid and AMY-2 is apparent visually. When AMY-2 was added to a β-amyloid system at a 1:1 ratio (50 μM each, room temperature), the solution rapidly turned opaque, indicating an interaction that produced a colloidal product. A solution of β-amyloid alone under the same conditions remained clear, and did not appear to produce a colloid.

Scanning probe microscopy (SPM) images further demonstrated the avidity of AMY-2 binding to β-Amyloid$_{1-40}$. SPM images were taken of adsorbed peptide material on a hydrophilic surface (mica or muscovite). The images (not shown) revealed large, amorphous aggregates of the interaction product of β-Amyloid and AMY-2. These non-fibrillar aggregates were ~100 nm in height and appeared as clusters of aggregated peptide material. By contrast, β-amyloid without AMY-2 displayed an abundance of spherical aggregates, around 3 nm in height with further early aggregate structures formed from linear associations of the spherical aggregates.

Another study to explore the later β-Amyloid aggregation (i.e., fibril formation) produced an image of elongated fibrils greater than 10 μm long and 8 nm high. By contrast, a sample containing a 1:1 ratio of 50 μM β-Amyloid and AMY-2 showed no fibril formation, and only amorphous aggregates of varying height.

Solid-Phase Peptide Synthesis with Sterically Hindered ααAAs and Modified Amino Acids Peptides for use in this invention may be synthesized in accordance with standard peptide synthesis techniques known in the art, modified where appropriate for more difficult couplings with ααAAs. Synthesis and couplings of ααAAs will be conducted as described in C. Wysong et al., "4-Aminopiperidine-4-carboxylic acid: A cyclic alpha, alpha-disubstitued amino acid for preparation of water-soluble highly helical peptides," *J. Org. Chem.*, vol. 61, pp. 7650-7651 (1996); T. Yokum et al., "Antimicrobial alpha, alpha-dialkylated amino acid rich peptides with in-vivo activity against an intracellular pathogen," *J. Med. Chem.*, vol. 39, pp. 3603-3605 (1996); T. Yokum et al., "Solvent effects on the 3$_{10}$/alpha-helix equilibrium in short amphipathic peptides rich in alpha, alpha-disubstituted amino acids," *J. Am. Chem. Soc.*, vol. 119, pp. 1167-1168 (1997); and T. Yokum et al., T. S., Elzer, P. H., and McLaughlin, M. L., "Antimicrobial peptides with activity against an intracellular pathogen," pp. 652-653 in J. Tam et al. (Eds.) *Peptides: Chemistry, Structure and Biology. Proceedings of the Fifteenth American Peptide Symposium*, Kluwer, Dordrecht, Netherlands (1999).

We have found that it often helps to heat these coupling reactions, especially those at the C-terminal of the peptide, using either preformed acid fluorides or in situ activation with HATU or PyAOP. See L. Carpino et al., "Synthesis of (9-Fluorenylmethyl)Oxy)Carbonyl (Fmoc) Amino-Acid Fluorides—Convenient New Peptide Coupling Reagents Applicable to the Fmoc/Tert-Butyl Strategy For Solution and Solid-Phase, *J. Am. Chem. Soc.*, vol. 112, pp. 9651-9652 (1990); and L. Carpino et al., "Advantageous Applications of Azabenzotriazole (Triazolopyridine)-Based Coupling Reagents to Solid-Phase Peptide-Synthesis," *Chem. Commun.*, pp. 201-203 (1994). We have, for example, completed the solid-phase synthesis of four peptides containing alternating Dpg residues using PyAOP for coupling on a 9050 peptide synthesizer. Without heating the coupling reactions, very poor results were obtained. But by heating the column jacket to 50° C. throughout the synthesis, we prepared the four peptides DPG1-DPG3 at high yield, peptides that were readily purified to homogeneity, with the expected masses as measured by MALDI-MS. DPG1: Ac-Lys-Dpg-Tyr-Dpg-Lys-NH$_2$; DPG2: Ac-Lys-Dpg-Tyr-Dpg-Glu-NH$_2$; DPG3: Ac-Glu-Dpg-Tyr-Dpg-Glu-NH$_2$; DPG4: H-Lys-Dpg-Val-Dpg-Thr-Dpg-Val-Glu-NH$_2$ (SEQ ID NO: 8).

We have obtained CD spectra for the peptides DPG1-DPG3 at 100 μM concentration in 10 mM phosphate buffer, 20° C., pH 7. The spectrum of DPG2 suggested significant β-sheet structure.

Synthesis of Novel ααAAs for Incorporation into Blocker Peptides

Synthesis of chiral ααAAs may be based upon the pig liver esterase (PLE) asymmetrization of the malonate, following the procedure of M. Schneider et al., *Angew. Chem. Int Ed. Engl.*, vol. 23, p. 66 (1984); and E. Schoffers et al., Enantioselective Synthesis Through Enzymatic Asymmetrization, *Tetrahedron*, vol. 52, pp. 3769-3826 (1996). First, alkylation of the monoalkylated malonate is achieved by Michael addition of the malonate anion to t-butylacrylate. PLE then selectively cleaves the pro-R methyl ester in a yield of 50-90%. A modified Curtius rearrangement with fluorenylmethanol following the procedure of K. Ninomiya et al, "Phosphorus in organic synthesis-VII: Diphenylphosphorylazide (DPPA). A new convenient reagent for a modified Curtius reaction," *Tetrahedron*, vol. 30, pp. 2151-2157 (1974) converts the free carboxylate into the protected α-amine functionality directly. Hydrolysis of the α-carboxylate ester gives the D-glutamate analog with a hydrophobic side-chain in the pro-S position. Alternatively, the γ-t-butyl ester may be removed with acid treatment and then converted to a Boc-protected amine by the Curtius rearrangement, which places a D-diaminobutanoic acid (Dab) derivative hydrophobic side-chain in the pro-S position. These amino acids should be excellent promoters of β-sheet secondary structure due to their large substituents and also due to the branching in their hydrophobic side-chains.

Cytoprotection from Aβ Aggregates by the Novel Inhibitors.

Control experiments will be conducted to validate the PC-12 cell in vitro assays results that we obtain. We will compare our cytotoxicity and cytoprotective effects with those that have been previously reported for other putative inhibitors. See, e.g., M. Pallitto et al., "Recognition sequence design for peptidyl modulators of beta-amyloid aggregation and toxicity," *Biochemistry*, vol. 38, pp. 3570-3578 (1999). We will compare results with Trypan Blue exclusion assay. We will determine if the novel inhibitors exhibit direct cytotoxicity, and if so, the minimum cytotoxic concentration for the inhibitors, which should be a concentration substantially below the cytoprotective concentrations. We will confirm the cytoprotective effect of the novel inhibitors over a range of absolute and relative concentrations in the presence of Aβ aggregates formed under standard conditions (i.e., those of Pallitto et al. (1999)).

Pharmaceutical Compositions

The invention also pertains to pharmaceutical compositions containing peptides in accordance with the present invention. In one embodiment, the composition includes such a peptide in a therapeutically or prophylactically effective amount, sufficient to inhibit or reduce aggregation of natural amyloid β-sheets, along with a pharmaceutically acceptable carrier. In another embodiment, the composition includes such a peptide in a therapeutically or prophylactically effective amount, sufficient to inhibit or reduce the neurotoxicity of natural amyloid peptides, and a pharmaceutically acceptable carrier. A therapeutically or prophylactically "effective amount" refers to an amount that is effective, when administered at dosages and for periods of time necessary, to achieve the desired therapeutic result, such as reduction, reversal, inhibition, or prevention of amyloid plaque deposition neurotoxicity. A therapeutically or prophylactically effective amount may vary according to factors such as the disease state, age, sex, and weight of the individual, and the ability of the peptide to elicit a desired response in a particular individual. Dosage regimens may be adjusted to provide the optimum response. An effective amount is also one in which any toxic or detrimental effects of the peptide are outweighed by the therapeutically beneficial effects. Typically, since a prophylactic dose is used in subjects prior to or at an earlier stage of disease, a prophylactically effective amount is less than a therapeutically effective amount.

Dosage regimens may be adjusted to provide the optimum response. For example, a single bolus may be administered, several divided doses may be administered over time, or the dose may be proportionally reduced or increased as indicated by the individual situation. It is especially advantageous to formulate injectable or parenteral compositions in dosage unit form for ease of administration and uniformity of dosage. Dosage unit form as used herein refers to physically discrete units suited as unitary dosages for the subjects to be treated; each unit containing a predetermined quantity of active peptide calculated to produce the desired therapeutic effect in association with the required pharmaceutical carrier. The specification for the dosage unit forms of the invention are dictated by and directly dependent on (a) the unique characteristics of the active peptide and the particular therapeutic effect to be achieved, and (b) the limitations inherent in the art of compounding such an active compound for the treatment of sensitivity in individuals.

As used herein a "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for injection or parenteral administration. In another embodiment, the carrier is suitable for administration into the central nervous system (e.g., intraspinally or intracerebrally). Alternatively, the carrier can be suitable for intravenous, intraperitoneal, or intramuscular administration. In another embodiment, the carrier is suitable for oral administration. Oral administration can be particularly advantageous in certain cases due to ease of administration. Furthermore, many peptides in accordance with the present invention are resistant to digestive enzymes, and those peptides are therefore particularly suited for oral administration.

In another embodiment, the carrier is suitable for intranasal or intra-lung administration. Intranasal administration can be particularly advantageous due to the ease of administration, ready absorption, bypass of the digestive system, and the observation that a significant concentration of drugs administered intranasally can be transported directed to the brain. See, e.g., R. Thorne et al., "Delivery of neurotrophic factors to the central nervous system—Pharmacokinetic considerations," *Clinic. Pharmacokinetics*, vol. 40, pp. 907-946 (2001); and J. Born et al., "Sniffing neuropeptides: a transnasal approach to the human brain," *Nature Neurosci.*, vol. 5, pp. 514-516 (2002).

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active peptide, the use thereof in the pharmaceutical compositions of the invention is contemplated. Supplementary active compounds can also be incorporated into the compositions.

Therapeutic compositions typically should be sterile and stable under the conditions of manufacture and storage. The composition can be formulated as a solution, microemulsion, liposome, or other ordered structure suitable for high drug concentration. The carrier may be a solvent or dispersion medium containing, for example, water, ethanol, a polyol (for example, glycerol, propylene glycol, liquid polyethylene glycol, and the like), and suitable mixtures thereof. The proper fluidity may be maintained, for example, by the use of a coating such as lecithin, by the maintenance of the required particle size in the case of dispersion, or by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Moreover, the peptides may be administered in a time release formulation, for example in a composition that includes a slow release polymer. The active compounds may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid, and polylactic, polyglycolic copolymers. Many methods for the preparation of such formulations are known to those skilled in the art.

Sterile injectable solutions can be prepared by incorporating the active peptide in an appropriate solvent with one or a combination of ingredients enumerated above, as required, followed by filtered sterilization. Generally, dispersions are prepared by incorporating the active peptide into a sterile vehicle that contains a dispersion medium and other ingredients such as those listed above. In the case of sterile powders for the preparation of sterile injectable solutions, preferred methods of preparation include vacuum drying and freeze-drying from a previously sterile-filtered solution to yield a powder of the active peptide plus any additional desired ingredients.

Optional drug delivery vehicles containing a cyclodextrin derivative for delivery of peptides to the central nervous system may be used, such as are described in Bodor, N., et al. (1992) Science 257:1698-1700.

In another embodiment, a pharmaceutical composition comprising a peptide in accordance with the present invention is formulated such that the peptide is transported across the blood-brain barrier (BBB). Various strategies known in the art for increasing transport across the BBB may be adapted to enhance transport across the BBB See e.g., Pardridge, W. M. (1994) Trends in Biotechnol. 12:239-245; Van Bree, J. B. et al. (1993) Pharm. World Sci. 15:2-9; and Pardridge, W. M. et al. (1992) Pharmacol. Toxicol. 71:3-10. In one approach, the peptide is chemically modified to form a prodrug with enhanced transmembrane transport. Suitable chemical modifications include covalent linkage of a fatty acid to the peptide through an amide or ester linkage, or glycation of the peptide. See, e.g., U.S. Pat. No. 4,933,324 and PCT Publication WO 89/07938, both by Shashoua; U.S. Pat. No. 5,284,876 by Hesse et al.; Toth, I. et al. (1994) J. Drug Target. 2:217-239; Shashoua, V. E. et al. (1984) J. Med. Chem. 27:659-664; and U.S. Pat. No. 5,260,308 by Poduslo et al., Also, N-acylamino acid derivatives may be used in a peptide to form a "lipidic" prodrug. See, e.g., U.S. Pat. No. 5,112,863 by Hashimoto et al.

In another approach for enhancing transport across the BBB, the peptide is conjugated to a second peptide or protein, thereby forming a chimeric protein, wherein the second peptide or protein undergoes absorptive-mediated or receptor-mediated transcytosis through the BBB. Accordingly, by coupling the peptide to this second peptide or protein, the chimeric protein is transported across the BBB. The second peptide or protein may be a ligand for a brain capillary endothelial cell receptor ligand. For example, the ligand may be a monoclonal antibody that specifically binds to the transferrin receptor on brain capillary endothelial cells. See, e.g., U.S. Pat. Nos. 5,182,107 and 5,154,924, and PCT Publications WO 93/10819 and WO 95/02421, all by Friden et al. Other peptides or proteins that can mediate transport across the BBB include histones and ligands such as biotin, folate, niacin, pantothenic acid, riboflavin, thiamin, pryridoxal and ascorbic acid. See, e.g., U.S. Pat. No. 4,902,505 by Pardridge and Schimmel, and U.S. Pat. Nos. 5,416,016 and 5,108,921, both by Heinstein. Additionally, the glucose transporter GLUT-1 has been reported to transport glycopeptides (L-serinyl-β-D-glucoside analogues of [Met5]enkephalin) across the BBB. See Polt, R. et al. (1994) Proc. Natl. Acad. Sci. USA 91:7114-1778. Accordingly, the novel peptides may be coupled to such a glycopeptide to target the peptide to the GLUT-1 glucose transporter. For example, a peptide that is modified at its amino terminus with the modifying group Aic (3-(O-aminoethyl-iso)-cholyl, a derivative of cholic acid having a free amino group) may be coupled to a glycopeptide through the amino group of Aic by standard methods. Chimeric proteins can be formed, at least in part, by recombinant DNA methods (e.g., by formation of a chimeric gene encoding a fusion protein) or by chemical crosslinking of the peptide to the second peptide or protein to form a chimeric protein. The couplings to the ααAAs would need to be made by alternative means, such as those previously described here. Numerous chemical crosslinking agents are known in the art. Some are commercially available, e.g., from Pierce (Rockford Ill.). A crosslinking agent may be chosen that allows for high yield coupling of the novel peptide to the second peptide or protein and for subsequent cleavage of the linker to release bioactive peptide. For example, a biotin-avidin-based linker system may be used.

In yet another approach for enhancing transport across the BBB, the peptide is encapsulated in a carrier vector that mediates transport across the BBB. For example, the peptide may be encapsulated in a liposome, such as a positively charged unilamellar liposome. See, e.g., PCT Publications WO 88/07851 and WO 88/07852, both by Faden. Or it may be encapsulated in polymeric microspheres. See, e.g., U.S. Pat. No. 5,413,797 by Khan et al., U.S. Pat. No. 5,271,961 by Mathiowitz et al., and U.S. Pat. No. 5,019,400 by Gombotz et al.). Moreover, the carrier vector may be modified to target it for transport across the BBB. For example, the carrier vector (e.g., liposome) may be covalently modified with a molecule that is actively transported across the BBB, or with a ligand for brain endothelial cell receptors, such as a monoclonal antibody that specifically binds to transferrin receptors. See, e.g., PCT Publications WO 91/04014 by Collins et al., and WO 94/02178 by Greig et al.

In still another approach to enhancing transport of the peptide across the BBB, the peptide is coadministered with another agent that functions to permeabilize the BBB. Examples of such BBB "permeabilizers" include bradykinin and bradykinin agonists. See e.g., U.S. Pat. No. 5,112,596 by Malfroy-Camine. Other examples include the peptidic compounds disclosed in U.S. Pat. No. 5,268,164 by Kozarich et al.

A peptide in accordance with this invention may be formulated into a pharmaceutical composition wherein the peptide is the only active compound; or, alternatively, the pharmaceutical composition may contain additional active compounds. For example, two or more peptides in accordance with this invention may be used in combination. Moreover, a peptide compound of the invention may be combined with one or more other agents that have anti-amyloidogenic properties. For example, a peptide compound may be combined with the non-specific cholinesterase inhibitor tacrine (COGNEX®, Parke-Davis).

In another embodiment, a pharmaceutical composition of the invention is provided as a packaged formulation. The packaged formulation may include a pharmaceutical composition of the invention in a container and printed instructions for administration of the composition for treating a subject having an amyloid disease, e.g. Alzheimer's disease.

In the method of the invention, natural amyloid peptides may be contacted with the novel peptides either in vitro or in vivo. Thus, the term "contacted with" is intended to encompass both incubation of a peptide with a natural Aβ preparation or other amyloid peptide in vitro and delivery of the peptide to a site in vivo where natural Aβ or other amyloid peptide is present.

Miscellaneous

Following further in vitro confirmation of the efficacy of the invention, the efficacy of the invention will be demonstrated in vivo, first in animal models, and then in humans, in accordance with applicable laws and regulations.

The complete disclosures of all references cited in this specification are hereby incorporated by reference. In the event of an otherwise irreconcilable conflict, however, the present specification shall control.

We claim:

1. A compound for inhibiting the toxicity of an amyloid protein or amyloid peptide, wherein the amyloid protein or amyloid peptide comprises an aggregation-inducing sequence of at least four modified or unmodified amino acids; said compound comprising a peptidyl sequence selected from the group consisting of:

$X_{aa1}—Y_{AA1}—X_{aa2}—Y_{AA2}—(S)_n$;

$(S)_n—X_{aa1}—Y_{AA1}—X_{aa2}—Y_{AA2}$;

$Y_{AA1}—X_{aa1}—Y_{AA2}—X_{aa2}—(S)_n$;

$(S)_n—Y_{AA1}—X_{aa1}—Y_{AA2}—X_{aa2}$;

$X_{aa1}—Y_{AA1}—X_{aa2}—Y_{AA2}—X_{aa3}—(S)_n$;

$(S)_n—X_{aa1}—Y_{AA1}—X_{aa2}—Y_{AA2}—X_{aa3}$;

$Y_{AA1}—X_{aa1}—Y_{AA2}—X_{aa2}—Y_{AA3}—(S)_n$;

$(S)_n—Y_{AA1}—X_{aa1}—Y_{AA2}—X_{aa2}—Y_{AA3}$;

$X_{aa1}—Y_{AA1}—X_{aa2}—Y_{AA2}—X_{aa3}—Y_{AA3}—(S)_n$;

$(S)_n—X_{aa1}—Y_{AA1}—X_{aa2}—Y_{AA2}—X_{aa3}—Y_{AA3}$;

$Y_{AA1}—X_{aa1}—Y_{AA2}—X_{aa2}—Y_{AA3}—X_{aa3}—(S)_n$; and $(S)_n—Y_{AA1}—X_{aa1}—Y_{AA2}—X_{aa2}—Y_{AA3}—X_{aa3}$;

wherein:

(a) $X_{aa1}$, $X_{aa2}$, and $X_{aa3}$ are natural or synthetic amino acids that are identical or homologous to alternating amino acids of the aggregation-inducing sequence of the amyloid protein or amyloid peptide, and that have side chains adapted for cross-strand side chain interactions with a β-sheet;

(b) $Y_{AA1}$, $Y_{AA2}$, and $Y_{AA3}$ are natural or synthetic amino acids that are identical or homologous to alternating amino acids of the aggregation-inducing sequence of the amyloid protein or amyloid peptide; wherein $Y_{AA1}$, $Y_{AA2}$, and $Y_{AA3}$ correspond to amino acids that will be positioned on opposite faces of a β-sheet containing the amino acids that correspond to $X_{aa1}$, $X_{aa2}$, and $X_{aa3}$; and wherein the amino acids in the amyloid protein or amyloid peptide that correspond to $X_{aa1}$, $X_{aa2}$, and $X_{aa3}$ alternate with the amino acids in the amyloid protein or amyloid peptide that correspond to $Y_{AA1}$, $Y_{AA2}$, and $Y_{AA3}$; wherein at least two of $Y_{AA1}$, $Y_{AA2}$, and $Y_{AA3}$ are $C^{\alpha,\alpha}$-disubstituted amino acids;

(c) $(S)_n$ is a hydrophilic region comprising hydrophilic amino acids or other hydrophilic groups; wherein n is from 4 to 10, and wherein said hydrophilic region has a size not larger than about the size of a decapeptide;

(d) either or both ends of said peptidyl sequence optionally comprise additional functionality that does not adversely affect the compound's ability to inhibit the toxicity of an amyloid protein or amyloid peptide, as compared to an otherwise identical compound lacking such additional functionality;

(e) the number of amino acids in the aggregation sequence of the amyloid protein or amyloid peptide may be the same as, or different from, the number of natural or synthetic amino acids in said peptidyl sequence; and (f) said compound is neither Lys-Dibg-Val-Dbzg-Phe-Dpg-(Lys)$_6$-NH$_2$ (SEQ ID NO: 4); nor Dpg-Phe-Dbzg-Val-Dibg-(Lys)$_7$-NH$_2$ (SEQ ID NO: 18); nor(Lys)$_6$-Dibg-Val-Dbzg-Phe-Dpg-Lys-NH$_2$ (SEQ ID NO: 19).

2. The compound of claim 1, wherein said compound is (Lys)$_7$-Dibg-Val-Dbzg-Phe-Dpg-NH$_2$ (SEQ ID NO: 5).

3. The compound of claim 1, wherein the aggregation-inducing sequence is selected from the group consisting of KLVFFA (SEQ ID NO: 3); FLVHS (SEQ ID NO: 9); NFLVH (SEQ ID NO: 10); NFGAIL (SEQ ID NO: 11); VGGAVVTGV (SEQ ID NO: 12); VNITIKQHTVTTTT (SEQ ID NO: 13); LANFLV (SEQ ID NO: 14); FLVHSS (SEQ ID NO: 15); AGDV (SEQ ID NO: 16); and Q$_m$; wherein m is an integer from 25 to 45.

4. The compound of claim 3, wherein the aggregation-inducing sequence is KLVFFA (SEQ ID NO: 3).

5. The compound of claim 3, wherein the aggregation-inducing sequence is FLVHS (SEQ ID NO: 9).

6. The compound of claim 3, wherein the aggregation-inducing sequence is NFLVH (SEQ ID NO: 10).

7. The compound of claim 3, wherein the aggregation-inducing sequence is NFGAIL (SEQ ID NO: 11).

8. The compound of claim 3, wherein the aggregation-inducing sequence is VGGAWTGV (SEQ ID NO: 12).

9. The compound of claim 3, wherein the aggregation-inducing sequence is GAV.

10. The compound of claim 3, wherein the aggregation-inducing sequence is VNITIKQHTVTTTT (SEQ ID NO: 13).

11. The compound of claim 3, wherein the aggregation-inducing sequence is LANFLV (SEQ ID NO: 14).

12. The compound of claim 3, wherein the aggregation-inducing sequence is FLVHSS (SEQ ID NO: 15).

13. The compound of claim 3, wherein the aggregation-inducing sequence is AGDV (SEQ ID NO: 16).

14. The compound of claim 3, wherein the aggregation-inducing sequence is $Q_m$; wherein m is an integer from 25 to 45.

15. The compound of claim 1, wherein each of $Y_{AA1}$, $Y_{AA2}$ and $Y_{AA3}$ is an $C^{\alpha,\alpha}$-disubstituted amino acids.

16. A composition of matter comprising the compound of claim 1, and a pharmaceutically acceptable carrier.

17. A compound as recited in claim 1, wherein the amyloid protein or amyloid peptide comprises an aggregation-inducing sequence of at least six modified or unmodified amino acids, and wherein said peptidyl sequence is selected from the group consisting of:

$(S)_n$—$X_{aa1}$—$Y_{AA1}$—$X_{aa2}$—$Y_{AA2}$—$X_{aa3}$—$Y_{AA3}$;

$Y_{AA1}$—$X_{aa1}$—$Y_{AA2}$—$X_{aa2}$—$Y_{AA3}$—$X_{aa3}$—$(S)_n$; and $(S)_n$—$Y_{AA1}$—$X_{aa1}$—$Y_{AA2}$—$X_{aa2}$—$Y_{AA3}$—$X_{aa3}$.

18. A compound as recited in claim 1, wherein the amyloid protein or amyloid peptide comprises an aggregation-inducing sequence of at least five modified or unmodified amino acids, and wherein said peptidyl sequence is selected from the group consisting of:

$X_{aa1}$—$Y_{AA1}$—$X_{aa2}$—$Y_{AA2}$—$X_{aa3}$—$(S)_n$;

$(S)_n$—$X_{aa1}$—$Y_{AA1}$—$X_{aa2}$—$Y_{AA2}$—$X_{aa3}$;

$Y_{AA1}$—$X_{aa1}$—$Y_{AA2}$—$X_{aa2}$—$Y_{AA3}$—$(S)_n$; and $(S)_n$—$Y_{AA1}$—$X_{aa1}$—$Y_{AA2}$—$X_{aa2}$—$Y_{AA3}$.

19. A compound comprising a peptidyl sequence selected from the group consisting of:

$X_{aa1}$—$Y_{AA1}$—$X_{aa2}$—$Y_{AA2}$—$X_{aa3}$—$Y_{AA3}$—$(S)_n$;

$(S)_n$—$X_{aa1}$—$Y_{AA1}$—$X_{aa2}$—$Y_{AA2}$—$X_{aa3}$—$Y_{AA3}$;

$Y_{AA1}$—$X_{aa1}$—$Y_{AA2}$—$X_{aa2}$—$Y_{AA3}$—$X_{aa3}$—$(S)_n$; and $(S)_n$—$Y_{AA1}$—$X_{aa1}$—$Y_{AA2}$—$X_{aa2}$—$Y_{AA3}$—$X_{aa3}$;

wherein:
- (a) $X_{aa1}$ is L-lysine or D-lysine, $X_{aa2}$ is L-valine or D-valine, and $X_{aa3}$ is L-phenylalanine or D-phenylalanine;
- (b) $Y_{AA1}$ is a $C^{\alpha,\alpha}$-disubstituted amino acid analog of leucine, $Y_{AA2}$ is a $C^{\alpha,\alpha}$-disubstituted amino acid analog of phenylalanine, and $Y_{AA3}$ is a $C^{\alpha,\alpha}$-disubstituted amino acid analog of alanine;
- (c) $(S)_n$ is a hydrophilic region comprising hydrophilic amino acids or other hydrophilic groups; and
- (d) said compound is not Lys-Dibg-Val-Dbzg-Phe-Dpg-(Lys)$_6$-NH$_2$ (SEQ ID NO: 4).

20. The compound of claim 1, wherein n is from 4 to 6.

21. The compound Lys-Dibg-Val-Dbzg-Phe-Dpg-(Lys)$_6$-NH$_2$ (SEQ ID NO: 4).

22. A compound selected from the group consisting of Lys-Dibg-Val-Dbzg-Phe-Dpg-Lys-NH$_2$ (SEQ ID NO: 6); and Lys-Dibg-Val-Dbzg-Phe-Dpg-NH$_2$ (SEQ ID NO: 7).

23. The compound of claim 22, wherein said compound is Lys-Dibg-Val-Dbzg-Phe-Dpg-Lys-NH$_2$ (SEQ ID NO: 6).

24. The compound of claim 22, wherein said compound is Lys-Dibg-Val-Dbzg-Phe-Dpg-NH$_2$ (SEQ ID NO: 7).

* * * * *

```
                          SEQUENCE LISTING

<160> NUMBER OF SEQ ID NOS: 17

<210> SEQ ID NO 1
<211> LENGTH: 5
<212> TYPE: PRT
<213> ORGANISM: Homo sapiens

<400> SEQUENCE: 1

Lys Leu Val Phe Phe
1               5

<210> SEQ ID NO 2
<211> LENGTH: 4
<212> TYPE: PRT
<213> ORGANISM: Homo sapiens

<400> SEQUENCE: 2

Lys Leu Val Phe
1

<210> SEQ ID NO 3
<211> LENGTH: 6
<212> TYPE: PRT
<213> ORGANISM: Homo sapiens

<400> SEQUENCE: 3

Lys Leu Val Phe Phe Ala
1               5

<210> SEQ ID NO 4
<211> LENGTH: 12
<212> TYPE: PRT
<213> ORGANISM: Artificial sequence
<220> FEATURE:
<223> OTHER INFORMATION: Designed peptide.  This is an engineered
      modification of SEQ ID NO: 3, which is in turn derived from Homo
      sapiens.
<220> FEATURE:
<221> NAME/KEY: MISC_FEATURE
<222> LOCATION: (2)..(2)
<223> OTHER INFORMATION: X in position 2 is C-alpha,alpha-
      diisobutylglycine.
<220> FEATURE:
<221> NAME/KEY: MISC_FEATURE
<222> LOCATION: (4)..(4)
<223> OTHER INFORMATION: X in position 4 is C-alpha,alpha-
      dibenzylglycine.
<220> FEATURE:
<221> NAME/KEY: MISC_FEATURE
<222> LOCATION: (6)..(6)
<223> OTHER INFORMATION: X in position 6 is C-alpha,alpha-
      dipropylglycine.
<220> FEATURE:
<221> NAME/KEY: MISC_FEATURE
```

```
<222> LOCATION: (12)..(12)
<223> OTHER INFORMATION: The Lys in position twelve is in amide form.

<400> SEQUENCE: 4

Lys Xaa Val Xaa Phe Xaa Leu Leu Leu Leu Leu Leu
1               5                   10

<210> SEQ ID NO 5
<211> LENGTH: 12
<212> TYPE: PRT
<213> ORGANISM: Artificial sequence
<220> FEATURE:
<223> OTHER INFORMATION: Designed peptide.  This is an engineered
      modification of SEQ ID NO: 3, which is in turn derived from Homo
      sapiens.
<220> FEATURE:
<221> NAME/KEY: misc_feature
<222> LOCATION: (8)..(8)
<223> OTHER INFORMATION: Xaa in position eight denotes C-alpha,alpha-
      diisobutylglycine.
<220> FEATURE:
<221> NAME/KEY: misc_feature
<222> LOCATION: (10)..(10)
<223> OTHER INFORMATION: Xaa in position ten denotes C-alpha,alpha-
      dibenzylglycine.
<220> FEATURE:
<221> NAME/KEY: misc_feature
<222> LOCATION: (12)..(12)
<223> OTHER INFORMATION: Xaa in position twelve denotes C-alpha,alpha-
      dipropylglycine amide.

<400> SEQUENCE: 5

Lys Lys Lys Lys Lys Lys Lys Xaa Val Xaa Phe Xaa
1               5                   10

<210> SEQ ID NO 6
<211> LENGTH: 7
<212> TYPE: PRT
<213> ORGANISM: Artificial sequence
<220> FEATURE:
<223> OTHER INFORMATION: Designed peptide.  This is an engineered
      modification of SEQ ID NO: 3, which is in turn derived from Homo
      sapiens.
<220> FEATURE:
<221> NAME/KEY: misc_feature
<222> LOCATION: (2)..(2)
<223> OTHER INFORMATION: Xaa in position two denotes C-alpha,alpha-
      diisobutylglycine.
<220> FEATURE:
<221> NAME/KEY: misc_feature
<222> LOCATION: (4)..(4)
<223> OTHER INFORMATION: Xaa in position four denotes C-alpha,alpha-
      dibenzylglycine.
<220> FEATURE:
<221> NAME/KEY: misc_feature
<222> LOCATION: (6)..(6)
<223> OTHER INFORMATION: Xaa in position six denotes C-alpha,alpha-
      dipropylglycine.
<220> FEATURE:
<221> NAME/KEY: misc_feature
<222> LOCATION: (7)..(7)
<223> OTHER INFORMATION: Lys in position seven is in amide form.

<400> SEQUENCE: 6

Lys Xaa Val Xaa Phe Xaa Lys
1               5

<210> SEQ ID NO 7
<211> LENGTH: 6
<212> TYPE: PRT
<213> ORGANISM: Artificial sequence
<220> FEATURE:
<223> OTHER INFORMATION: Designed peptide.  This is an engineered
```

```
        modification of SEQ ID NO: 3, which is in turn derived from Homo
        sapiens.
<220> FEATURE:
<221> NAME/KEY: misc_feature
<222> LOCATION: (2)..(2)
<223> OTHER INFORMATION: Xaa in position two denotes C-alpha,alpha-
        diisobutylglycine.
<220> FEATURE:
<221> NAME/KEY: misc_feature
<222> LOCATION: (4)..(4)
<223> OTHER INFORMATION: Xaa in position four denotes C-alpha,alpha-
        dibenzylglycine.
<220> FEATURE:
<221> NAME/KEY: misc_feature
<222> LOCATION: (6)..(6)
<223> OTHER INFORMATION: Xaa in position six denotes C-alpha,alpha-
        dibenzylglycine amide.

<400> SEQUENCE: 7

Lys Xaa Val Xaa Phe Xaa
1               5

<210> SEQ ID NO 8
<211> LENGTH: 8
<212> TYPE: PRT
<213> ORGANISM: Artificial sequence
<220> FEATURE:
<223> OTHER INFORMATION: Designed peptide.  This is an engineered
        modification of SEQ ID NO: 3, which is in turn derived from Homo
        sapiens.
<220> FEATURE:
<221> NAME/KEY: misc_feature
<222> LOCATION: (2)..(2)
<223> OTHER INFORMATION: Xaa in position two denotes C-alpha,alpha-
        dipropylglycine.
<220> FEATURE:
<221> NAME/KEY: misc_feature
<222> LOCATION: (4)..(4)
<223> OTHER INFORMATION: Xaa in position four denotes C-alpha,alpha-
        dipropylglycine.
<220> FEATURE:
<221> NAME/KEY: misc_feature
<222> LOCATION: (6)..(6)
<223> OTHER INFORMATION: Xaa in position six denotes C-alpha,alpha-
        dipropylglycine.
<220> FEATURE:
<221> NAME/KEY: misc_feature
<222> LOCATION: (8)..(8)
<223> OTHER INFORMATION: Glu in position 8 is in amide form.

<400> SEQUENCE: 8

Lys Xaa Val Xaa Thr Xaa Val Glu
1               5

<210> SEQ ID NO 9
<211> LENGTH: 5
<212> TYPE: PRT
<213> ORGANISM: Homo sapiens

<400> SEQUENCE: 9

Phe Leu Val His Ser
1               5

<210> SEQ ID NO 10
<211> LENGTH: 5
<212> TYPE: PRT
<213> ORGANISM: Homo sapiens

<400> SEQUENCE: 10

Asn Phe Leu Val His
1               5
```

-continued

```
<210> SEQ ID NO 11
<211> LENGTH: 6
<212> TYPE: PRT
<213> ORGANISM: Homo sapiens

<400> SEQUENCE: 11

Asn Phe Gly Ala Ile Leu
1               5

<210> SEQ ID NO 12
<211> LENGTH: 9
<212> TYPE: PRT
<213> ORGANISM: Homo sapiens

<400> SEQUENCE: 12

Val Gly Gly Ala Val Val Thr Gly Val
1               5

<210> SEQ ID NO 13
<211> LENGTH: 14
<212> TYPE: PRT
<213> ORGANISM: Homo sapiens

<400> SEQUENCE: 13

Val Asn Ile Thr Ile Lys Gln His Thr Val Thr Thr Thr Thr
1               5                   10

<210> SEQ ID NO 14
<211> LENGTH: 6
<212> TYPE: PRT
<213> ORGANISM: Homo sapiens

<400> SEQUENCE: 14

Leu Ala Asn Phe Leu Val
1               5

<210> SEQ ID NO 15
<211> LENGTH: 6
<212> TYPE: PRT
<213> ORGANISM: Homo sapiens

<400> SEQUENCE: 15

Phe Leu Val His Ser Ser
1               5

<210> SEQ ID NO 16
<211> LENGTH: 4
<212> TYPE: PRT
<213> ORGANISM: Homo sapiens

<400> SEQUENCE: 16

Ala Gly Asp Val
1

<210> SEQ ID NO 17
<211> LENGTH: 6
<212> TYPE: PRT
<213> ORGANISM: Artificial
<220> FEATURE:
<223> OTHER INFORMATION: Designed peptide.  This is an engineered
      modification of SEQ ID NO: 3, which is in turn derived from Homo
      sapiens.
<220> FEATURE:
<221> NAME/KEY: misc_feature
<222> LOCATION: (2)..(2)
<223> OTHER INFORMATION: Xaa in position two denotes C-alpha,alpha-
```

```
        diisobutylglycine.
<220> FEATURE:
<221> NAME/KEY: misc_feature
<222> LOCATION: (4)..(4)
<223> OTHER INFORMATION: Xaa in position four denotes C-alpha,alpha-
        dibenzylglycine.
<220> FEATURE:
<221> NAME/KEY: misc_feature
<222> LOCATION: (6)..(6)
<223> OTHER INFORMATION: Lys in position six is in amide form.

<400> SEQUENCE: 17

Lys Xaa Val Xaa Phe Lys
1               5
```